US012616938B2

(12) United States Patent
Lim et al.

(10) Patent No.: US 12,616,938 B2
(45) Date of Patent: May 5, 2026

(54) FILTER DEVICE FOR DIALYSIS APPLICATIONS

(71) Applicant: AWAK TECHNOLOGIES PTE LTD, Singapore (SG)

(72) Inventors: Jason Tze Chern Lim, Singapore (SG); Peter Haywood, Singapore (SG); Suresha Belur Venkataraya, Singapore (SG); Joel Preetham Fernandes, Singapore (SG); Daniel Wei Teik Tan, Singapore (SG); Yue Wang, Singapore (SG); Abel Samson Dsouza, Singapore (SG); Wenhui Dennis Ong, Singapore (SG); Sanjay Kumar Singh, Singapore (SG)

(73) Assignee: AWAK TECHNOLOGIES PTE LTD, Singapore (SG)

( * ) Notice: Subject to any disclaimer, the term of this patent is extended or adjusted under 35 U.S.C. 154(b) by 447 days.

(21) Appl. No.: 18/003,588

(22) PCT Filed: Jun. 28, 2021

(86) PCT No.: PCT/SG2021/050375
§ 371 (c)(1),
(2) Date: Dec. 28, 2022

(87) PCT Pub. No.: WO2022/005399
PCT Pub. Date: Jan. 6, 2022

(65) Prior Publication Data
US 2023/0256149 A1 Aug. 17, 2023

(30) Foreign Application Priority Data

Jul. 1, 2020 (SG) ............................ 10202006354R
Sep. 29, 2020 (GB) ....................................... 2015365

(51) Int. Cl.
*A61M 1/16* (2006.01)
*B01D 63/02* (2006.01)

(52) U.S. Cl.
CPC ............. *B01D 63/02* (2013.01); *A61M 1/165* (2014.02); *A61M 1/1658* (2013.01);
(Continued)

(58) Field of Classification Search
CPC .. A61M 1/165; A61M 1/1672; A61M 1/1696; A61M 1/287
See application file for complete search history.

(56) References Cited

U.S. PATENT DOCUMENTS 5,944,684 A * 8/1999 Roberts ................. A61M 1/281
604/28
6,234,991 B1 * 5/2001 Gorsuch ................ B01D 61/28
210/321.62
(Continued)

FOREIGN PATENT DOCUMENTS

DE 4027531 C1 7/1991
EP 0419234 A2 3/1991
(Continued)

OTHER PUBLICATIONS

Williams, Jennifer, European International Search Report for PCT/SG2021/050375; dated Jan. 20, 2022; 7 pages.
(Continued)

*Primary Examiner* — Rebecca E Eisenberg
*Assistant Examiner* — Ted Yang
(74) *Attorney, Agent, or Firm* — Daniel A. Thomson; Emerson Thomson Bennett, LLC

(57) ABSTRACT

The current invention relates to a peritoneal dialysis filter device, which comprises a housing comprising a first port and a second port, and a hollow fibre membrane formed from hollow hydrophilic fibres within the housing. When in
(Continued)

(a) 130 120 100 110 190
(b) 130 120 100 110 190
(c) 130 120 100 110 190

→ Dialysate flow path
---- Closed dialysate path use, a dialysate from a subject enters the filter device through the first port and exits via the second port in an outflow direction, and a regenerated dialysate from a sorbent system enters the filter device through the second port and exits via the first port in an inflow direction. Also disclosed herein is a peritoneal dialysis system comprising said filter device, a method for controlling dialysate flow in a peritoneal dialysis system, and a haemodialysis device.

4 Claims, 20 Drawing Sheets

(52) U.S. Cl.
CPC ........ *A61M 1/1672* (2014.02); *A61M 1/1696* (2013.01); *B01D 2325/36* (2013.01)

(56) References Cited

U.S. PATENT DOCUMENTS

| | | | |
|---|---|---|---|
| 7,622,041 B2 | 11/2009 | Dannenmaier et al. | |
| 9,254,355 B2 * | 2/2016 | Sandford | A61M 1/28 |
| 10,155,076 B2 * | 12/2018 | Merchant | A61M 1/14 |
| 10,232,103 B1 * | 3/2019 | Karoor | B01J 20/28052 |
| 2005/0006296 A1 * | 1/2005 | Sullivan | A61M 1/262 |
| | | | 210/512.1 |
| 2010/0217181 A1 * | 8/2010 | Roberts | A61M 1/1696 |
| | | | 604/29 |
| 2010/0312174 A1 * | 12/2010 | Hoffman | A61M 1/155 |
| | | | 604/29 |
| 2011/0303590 A1 * | 12/2011 | Childers | A61M 1/166 |
| | | | 210/96.2 |
| 2012/0271227 A1 | 10/2012 | Roberts et al. | |
| 2016/0325037 A1 | 11/2016 | Updyke et al. | |
| 2016/0339159 A1 * | 11/2016 | Nosaka | A61M 1/0281 |
| 2017/0189601 A1 * | 7/2017 | Cicchello | A61M 1/1601 |
| 2017/0281847 A1 * | 10/2017 | Manda | C02F 1/444 |
| 2017/0291144 A1 | 10/2017 | Schmittel et al. | |
| 2017/0340794 A1 | 11/2017 | Hahne et al. | |
| 2018/0021695 A1 * | 1/2018 | Ash | B01D 15/02 |
| | | | 210/287 |
| 2018/0147338 A1 | 5/2018 | Bluchel et al. | |

| | | | |
|---|---|---|---|
| 2021/0369930 A1 * | 12/2021 | Gura | A61M 1/1696 |
| 2022/0016328 A1 * | 1/2022 | Gura | B01D 15/08 |
| 2023/0256149 A1 * | 8/2023 | Lim | B01D 63/032 |
| | | | 604/6.09 |

FOREIGN PATENT DOCUMENTS

| | | | | |
|---|---|---|---|---|
| EP | 0980685 | A2 | 2/2000 | |
| EP | 1518564 | B1 | 3/2005 | |
| EP | 3031483 | A1 * | 6/2016 | A61M 1/1647 |
| JP | H0386218 | A | 4/1991 | |
| JP | 2009525071 | A | 7/2009 | |
| JP | 2012125537 | A | 7/2012 | |
| JP | 2014500067 | A | 1/2014 | |
| JP | 6456034 | B2 | 1/2019 | |
| WO | 2015006296 | A1 | 1/2015 | |
| WO | 2015177606 | A1 | 11/2015 | |

OTHER PUBLICATIONS

Agar, John Wm; "Review: Understanding sorbent dialysis systems;" Nephrology, vol. 15, No. 4, Jun. 1, 2010; pp. 406-411.

Williams, Jennifer; European Written Opinion for PCT/SG2021/050375; dated Jan. 20, 2022; 41 pages.

Williams, Jennifer, International Preliminary Report on Patentability (Chapter II) for PCT/SG2021/050375; dated Nov. 11, 2022; 35 pages.

Extracorporeal Life Support Organization (ELSO), "Guidelines for Adult Respiratory Failure," Version 1.4, Aug. 2017, 32 pages.

Sabrina Haroon; "Choosing a dialyzer: What clinicians need to know," Hemodialysis International, 2018, 22, S65-S74.

James F. Winchester; "The Potential Application of Sorbents in Peritoneal Dialysis"; Ronco C, Dell'Aquila R, Rodighiero MP (eds): Peritoneal Dialysis: A Clinical Update; Contrib Nephrol. Basel, Karger, 2006, vol. 150, pp. 336-343.

Yee Kang ONG; Singapore Search Report for SG10202006354R; dated Aug. 20, 2020; 4 pages.

UK Search Report for GB2015365.6; dated Nov. 11, 2020; 4 pages.

Examiner Michael Knight; United Kingdom Examination Report for GB2015365.6 dated Jun. 24, 2024.

A Japanese Office Action dated Mar. 19, 2025, issued in counterpart Japanese Application No. 2023-524483, is submitted herewith.

A European Search Report dated Feb. 21, 2025, in EP application No. 21 740.272.6-1014.

\* cited by examiner

→ Dialysate flow path

--- Closed dialysate path (a)

1000    1070    1074    1010

1092

1040

1033

1022

1060

1020

1030

1050

1032

1023

O₂

1024    1021    1072

1093

1071

1091

Blood flow

Dialysate flow

Gas flow (b)

1000    1074    1070

1060    1050

1030    1020

1033    1022

FILTER DEVICE FOR DIALYSIS APPLICATIONS

FIELD OF INVENTION

The current invention relates to the field of a filter device for peritoneal dialysis and haemodialysis. Also disclosed herein are dialysis systems and methods that make use of said filters.

BACKGROUND

The listing or discussion of a prior-published document in this specification should not necessarily be taken as an acknowledgement that the document is part of the state of the art or is common general knowledge.

Peritoneal dialysis (PD) is a type of dialysis which uses the peritoneum in a subject's abdomen as a membrane through which mass transfer of fluid and solutes occurs between dialysate and blood. This process is used to remove excess fluid, correct electrolyte and acid-base imbalances, and remove toxins in treatment of patients with kidney failure.

In peritoneal dialysis, dialysate (a solution typically containing sodium chloride, sodium hydrogen carbonate/sodium lactate, and an osmotic agent) is introduced through a permanent tube in the lower abdomen, is allowed to dwell for a certain period of time and is then removed. This may either occur at regular intervals throughout the day, known as continuous ambulatory peritoneal dialysis (CAPD), or at night with the assistance of a machine, known as automated peritoneal dialysis (APD). Compared to haemodialysis, PD allows greater patient mobility, produces fewer swings in symptoms due to its continuous nature, and is inherently safer as it does not rely on extracorporeal circulation of the patient's blood.

However, due to the oncotic pressure gradient in systems for peritoneal dialysis, proteins excreted by the subject are transported into the subject's peritoneum, where they mix together with toxins and electrolytes present in the dialysate fluid. There are multiple issues associated with this mixing. These include:

(a) the fact that this mixing leads to significant protein loss from the subject over long-term peritoneal dialysis treatment; and (b) as proteins are relatively large in size, the proteins can get trapped inside the sorbent system (when such a system is used to remove toxins), thereby affecting sorbent efficiency.

Additional problems that can be encountered with conventional PD systems include, but are not limited to the following.

(1) In sorbent-based dialysis systems, such as the REDY system, $CO_2$ produced during dialysate regeneration can become a health risk (hypercapnia) to patients with respiratory failure, and accumulated $CO_2$ bubbles can compromise the effective surface area of the hollow fibres used in the REDY system, thereby diminishing their performance and dialysis efficiency. In sorbent dialysis, urea-laden dialysate flows through urease, where urea is hydrolysed to ammonium and bicarbonate. Zirconium phosphate adsorbs cations such as the ammonium ion, releasing sodium and hydrogen ions, with the hydrogen ions then reacting with bicarbonate to form $CO_2$. In a closed-loop system without active degassing, such as the REDY system, this can lead to accumulation of potentially hazardous levels of $pCO_2$ in dialysate and returned blood. While ordinary patients are apparently able to exhale excess $CO_2$ with no adverse symptoms, patients with compromised respiratory systems were left in a hypercapnic, acidotic state. Therefore, conventional sorbent dialysis systems do not provide an effective $CO_2$ removal mechanism and are dependent on the patients' breathing to compensate for the increased serum $pCO_2$. Additionally, increased dialysate $pCO_2$ can lead to spontaneous bubble formation, and the bubbles are prone to accumulate in the filter. Conventional filters in sorbent dialysis do not include a provision for bubble removal, hence the need for manual intervention to "burp the dialyzer" (the technical term used), and prevent loss of dialysis surface area and underdialysis. Besides routine kidney dialysis, $CO_2$ removal is also a useful feature needed for dialysis in the acute care setting, for example in intensive care units (ICU). Current treatments use separate machines to deliver dialysis and for serum oxygenation/$CO_2$ removal.

(2) Protein-bound uremic toxins (PBUTs) have been implicated in numerous deleterious effects in chronic kidney disease (CKD) patients, as well as in end-stage renal disease (ESRD) patients. There is growing literature evidence suggesting that improving the dialytic removal of PBUTs can improve the outcomes for HD/PD patients. Methods have been proposed to remove PBUTs in both HD and PD systems. However, none of these methods have been proven on patients or integrated into existing devices. One of the main reasons why this has not occurred is that many of the solutions propose adding an albumin binder competitor into the dialysate solution, which alters the dialysate composition—and potentially alters the patient's serum composition. Therefore, these solutions are currently considered to be a drug and are therefore required to undergo rigorous clinical trials and regulatory processes before they can be approved for use.

(3) Proteins that become trapped inside filters during dialysis may clog the filter and compromise filtration by impeding the flow rate of the system and by reducing the surface area available for filtration. The end product of this may be a reduction in therapeutic efficacy. Additionally, in the case of an infection, the flow path may also be impacted in a similar manner by an increase in excreted leukocytes. Lastly, in conventional peritoneal dialysis methods, excreted proteins are discarded together with the drain fluid, which causes a significant loss of protein in a subject over the long-term. This can lead to malnutrition in a subject undergoing PD—further exacerbating the nutritional balance in which many PD patients are already compromised.

Thus, there remains a need for improved peritoneal dialysis systems that overcome some or all of the problems identified above.

SUMMARY OF INVENTION

1. A peritoneal dialysis filter device, which comprises:
   a housing comprising a first port and a second port; and
   a hollow fibre membrane formed from hollow hydrophilic fibres within the housing, where each of the fibres have an inner surface and an outer surface, wherein
   the inner surface of the hollow hydrophilic fibres are aligned co-axially with respect to the alignment of the first port and the outer surface of the hollow fibres is aligned perpendicularly with respect to the alignment of the second port, such that, when used:

a dialysate from a subject enters the filter device through the first port and exits via the second port in an outflow direction; and a regenerated dialysate from a sorbent system enters the filter device through the second port and exits via the first port in an inflow direction.

2. The peritoneal dialysis filter device according to Clause 1, wherein the device further comprises a post-filtration system, which comprises:

a first fluid pathway;

a second fluid pathway, which comprises a post-filtration sorbent compartment; and a switch for selecting between the first and second fluid pathways, where the first and second fluid pathways are both fluidly connected to the first port of the housing via the switch, where the sorbent compartment comprises a post-filtration sorbent that is suitable for removing one or more of water-soluble uremic toxins, protein-bound uremic toxins, low-molecular weight proteins, endotoxins, exotoxins, inflammatory mediators and microorganisms.

3. A peritoneal dialysis filter device, which comprises:

a housing comprising:

a first compartment having a first port, and a second port;

a second compartment, having a third port, an inlet port and an outlet port;

a switching means or apparatus fluidly connected to the first and third ports;

a head-space cavity portion that fluidly connects the first compartment to the second compartment;

a first hollow fibre membrane formed from hollow hydrophilic fibres within the first compartment of the housing, where each of the fibres have an inner surface and an outer surface and where the inner surface of the hollow hydrophilic fibres are aligned co-axially with respect to the alignment of the first port and the outer surface of the hollow fibres is aligned perpendicularly with respect to the alignment of the second port; and a second hollow fibre membrane formed from hollow hydrophobic fibres within the second compartment of the housing, where each of the fibres have an inner surface and an outer surface, where the inner surface of the hollow hydrophobic fibres are aligned co-axially with respect to the alignment of the third port and the outer surface of the hollow fibres is aligned perpendicularly with respect to the alignment of the inlet and/or outlet ports, such that, when in use:

a dialysate from a subject enters the first compartment of the filter device through the first port and exits the first compartment of the filter device via the second port in an outflow direction; and a regenerated dialysate from a sorbent system enters the first compartment of the filter device through the second port, passes through the head-space cavity into the second compartment, where the hollow hydrophobic fibres degasses the regenerated dialysate before it exits through the third port, with the removed gas exiting the system via the outlet port.

4. The peritoneal dialysis filter device according to Clause 3, wherein the device further comprises a post-filtration system, which comprises:

(a) a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

5. A peritoneal dialysis filter device, which comprises:

a housing comprising:

a first compartment having a first port, and a second port;

a second compartment, having a third port, a fourth port, an inlet port and an outlet port;

a switching means or apparatus fluidly connected to the first and third ports;

a first hollow fibre membrane formed from hollow hydrophilic fibres within the first compartment of the housing, where each of the fibres have an inner surface and an outer surface and where the inner surface of the hollow hydrophilic fibres are aligned co-axially with respect to the alignment of the first port and the outer surface of the hollow fibres is aligned perpendicularly with respect to the alignment of the second port; and a second hollow fibre membrane formed from hollow hydrophobic fibres within the second compartment of the housing, where each of the fibres have an inner surface and an outer surface, where the inner surface of the hollow hydrophobic fibres are aligned co-axially with respect to the alignment of the third and fourth ports and the outer surface of the hollow fibres is aligned perpendicularly with respect to the alignment of the inlet and/or outlet ports.

6. The peritoneal dialysis filter device according to Clause 5, wherein the device further comprises a post-filtration system, which:

(a) comprises a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) further comprises a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

7. A peritoneal dialysis system, comprising, a filter device;

a sorbent device, wherein the filter device is arranged to receive and filter the entirety of dialysate from a subject and to provide the filtered dialysate to the sorbent device when operated in an outflow direction; and the filter device is arranged to receive at least part of a regenerated dialysate from the sorbent device when operated in an inflow direction.

8. The peritoneal dialysis system according to Clause 7, wherein the filter device comprises:

a housing comprising a first port and a second port; and a hollow fibre membrane formed from hollow hydrophilic fibres within the housing, where each of the fibres have an inner surface and an outer surface, wherein the inner surface of the hollow hydrophilic fibres are aligned co-axially with respect to the first port and the outer surface of the hollow fibres is aligned perpendicularly with respect to the second port, such that, when used:

a dialysate from a subject enters the filter device through the first port and exits via the second port in an outflow direction; and a regenerated dialysate from the sorbent device enters the filter device through the second port and exits via the first port in an inflow direction.

9. The peritoneal dialysis system according to Clause 8, wherein the filter device further comprises a post-filtration system, which comprises:

a first fluid pathway;

a second fluid pathway, which comprises a post-filtration compartment; and a switch for selecting between the first and second fluid pathways, where the first and second fluid pathways are both fluidly connected to the first port of the housing via the switch, where the sorbent compartment comprises a post-filtration sorbent that is suitable for removing one or more of water-soluble uremic toxins, protein-bound uremic toxins, low-molecular weight proteins, endotoxins, exotoxins, inflammatory mediators and microorganisms.

10. The peritoneal dialysis system according to Clause 7, wherein the filter device comprises:

a housing comprising:

a first compartment having a first port, and a second port;

a second compartment, having a third port, an inlet port and an outlet port;

a switching means or apparatus fluidly connected to the first and third ports;

a head-space cavity portion that fluidly connects the first compartment to the second compartment;

a first hollow fibre membrane formed from hollow hydrophilic fibres within the first compartment of the housing, where each of the fibres have an inner surface and an outer surface and where the inner surface of the hollow hydrophilic fibres are aligned co-axially with respect to the alignment of the first port and the outer surface of the hollow fibres is aligned perpendicularly with respect to the alignment of the second port; and a second hollow fibre membrane formed from hollow hydrophobic fibres within the second compartment of the housing, where each of the fibres have an inner surface and an outer surface, where the inner surface of the hollow hydrophobic fibres are aligned co-axially with respect to the alignment of the third port and the outer surface of the hollow fibres is aligned perpendicularly with respect to the alignment of the inlet and/or outlet ports, such that, when in use:

a dialysate from a subject enters the first compartment of the filter device through the first port and exits the first compartment of the filter device via the second port in an outflow direction; and a regenerated dialysate from the sorbent device enters the first compartment of the filter device through the second port, passes through the head-space cavity into the second compartment, where the hollow hydrophobic fibres degasses the regenerated dialysate before it exits through the third port, with the removed gas exiting the system via the outlet port.

11. The peritoneal dialysis system according to Clause 10, wherein the filter device further comprises a post-filtration system, which comprises:

(a) a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) further comprises a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

12. The peritoneal dialysis system according to Clause 10 or Clause 11, wherein the system further comprises a bypass means or apparatus, which comprises:

(a) a bypass fluid pathway connected to the sorbent device and arranged to return a regenerated dialysate to the subject without passing through any part of the filter device; and a switching means or apparatus that selects between sending a regenerated dialysate to the filter device or to the bypass fluid pathway; or (b) a bypass fluid pathway connected to the sorbent device and arranged to return a regenerated dialysate to the subject which passes through the second compartment of the filter device, which comprises a fourth port, such that the dialysate enters the second compartment through the fourth port and exits through the third port; and a switching means or apparatus that selects between sending a regenerated dialysate to the second port or fourth port of filter device.

13. The peritoneal dialysis system according to Clause 7, wherein the filter device comprises:

a housing comprising:

a first compartment having a first port, and a second port;

a second compartment, having a third port, a fourth port, an inlet port and an outlet port;

a switching means or apparatus fluidly connected to the first and third ports;

a first hollow fibre membrane formed from hollow hydrophilic fibres within the first compartment of the housing, where each of the fibres have an inner surface and an outer surface and where the inner surface of the hollow hydrophilic fibres are aligned co-axially with respect to the alignment of the first port and the outer surface of the hollow fibres is aligned perpendicularly with respect to the alignment of the second port; and a second hollow fibre membrane formed from hollow hydrophobic fibres within the second compartment of the housing, where each of the fibres have an inner surface and an outer surface, where the inner surface of the hollow hydrophobic fibres are aligned co-axially with respect to the alignment of the third and fourth ports and the outer surface of the hollow fibres is aligned perpendicularly with respect to the alignment of the inlet and/or outlet ports.

14. The peritoneal dialysis system according to Clause 13, wherein the filter device further comprises a post-filtration system, which:

(a) comprises a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) further comprises a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

15. The peritoneal dialysis system according to Clause 13 or Clause 14, wherein the system further comprises a bypass means or apparatus, which comprises:

(a) a bypass fluid pathway connected to the sorbent device and arranged to return a regenerated dialysate to the subject without passing through any part of the filter device; and a switching means or apparatus that selects between sending a regenerated dialysate to the filter device or to the bypass fluid pathway; or (b) a bypass fluid pathway connected to the sorbent device and arranged to return a regenerated dialysate to the subject which passes through the second compartment of the filter device, such that the dialysate enters the second compartment through the fourth port and exits through the third port; and a switching means or apparatus that selects between sending a regenerated dialysate to the second port or fourth port of filter device.

16. The peritoneal dialysis system according to any one of Clauses 7 to 9, 10 to 12 and 13 to 15, wherein the system further comprises a bypass means or apparatus, which comprises:

a bypass fluid pathway connected to the sorbent device and arranged to return a regenerated dialysate to the subject without passing through the filter device; and a switching means or apparatus that selects between sending a regenerated dialysate to the filter device or to the bypass fluid pathway.

17. A method of peritoneal dialysis using a peritoneal dialysis system as described in any one of Clauses 7 to 16, the method comprising the steps of (a) connecting a subject to a peritoneal dialysis system as described in any one of Clauses 7 to 16; and (b) operating the system, such that:

in an outflow direction, dialysate is withdrawn from the peritoneum of the subject and passes through the filter device before passing to the sorbent device to provide a regenerated dialysate; and in an inflow direction, the regenerated dialysate is returned to the peritoneum of the subject, wherein at least part of the regenerated dialysate passes through the hydrophilic fibres of the filter device.

18. The method according to Clause 17, wherein the peritoneal dialysis system is as described in Clause 10, such that a first portion of the regenerated dialysate passes through the hydrophilic fibres of the filter device and a second portion of the regenerated dialysate passes through the bypass means or apparatus in the inflow direction.

19. The method according to Clause 17, wherein the peritoneal dialysis system is as described in Clause 16, such that a first portion of the regenerated dialysate passes through the hydrophilic fibres of the filter device and a second portion of the regenerated dialysate passes through the bypass means or apparatus in the inflow direction.

20. A haemodialysis device, which comprises:

a housing comprising:

an exchange compartment having a blood inlet port, and a dialysate inlet port and a dialysate outlet port;

a blood degassing compartment having a blood outlet port, a degassing gas inlet port and a negative pressure/gas outlet port;

a head-space cavity portion that fluidly connects the exchange compartment to the blood degassing compartment;

a first hollow fibre membrane formed from hollow hydrophilic fibres within the exchange compartment of the housing, where each of the fibres have an inner surface and an outer surface and where the inner surface of the hollow hydrophilic fibres are aligned co-axially with respect to the alignment of the blood inlet port and the outer surface of the hollow fibres is aligned perpendicularly with respect to the alignment of the dialysate inlet and outlet ports;

a second hollow fibre membrane formed from hollow hydrophobic fibres within the blood degassing compartment of the housing, where each of the fibres have an inner surface and an outer surface, where the inner surface of the hollow hydrophobic fibres are aligned co-axially with respect to the alignment of the blood outlet port and the outer surface of the hollow fibres is aligned perpendicularly with respect to the alignment of the gas inlet and/or negative pressure ports.

21. A haemodialysis device, which comprises:

a housing comprising:

an exchange compartment having a blood inlet port, a blood outlet port and a dialysate outlet port;

a dialysate degassing compartment having a dialysate inlet port, a degassing gas inlet port and a negative pressure/gas outlet port;

a wall defining a fluid-impermeable boundary between the exchange compartment and the dialysate degassing compartment;

a dialysate fluid portal allowing a dialysate to move from the dialysate degassing compartment to the exchange compartment;

a first hollow fibre membrane formed from hollow hydrophilic fibres within the exchange compartment of the housing, where each of the fibres have an inner surface and an outer surface and where the inner surface of the hollow hydrophilic fibres are aligned co-axially with respect to the alignment of the blood inlet and outlet ports, and the outer surface of the hollow fibres is aligned perpendicularly with respect to the alignment of the dialysate outlet port; and a second hollow fibre membrane formed from hollow hydrophobic fibres within the dialysate degassing compartment of the housing, where each of the fibres have an inner surface and an outer surface, where the inner surface of the hollow hydrophobic fibres are aligned co-axially with respect to the alignment of the degassing gas inlet port and the negative pressure/gas outlet port, and the outer surface of the hollow fibres is aligned perpendicularly with respect to the alignment of the dialysate inlet port and the dialysate fluid portal.

22. The device according to Clause 21, wherein:
(a) the dialysate fluid portal is located in the wall; and/or
(b) the device further comprises a device for regenerating dialysate.

23. A haemodialysis device, which comprises:
  a housing comprising:
    an exchange compartment having a blood inlet port, a blood outlet port, a first dialysate inlet port and a first dialysate outlet port;
    a dialysate degassing compartment having a second dialysate inlet port, a second dialysate outlet port, a degassing gas inlet port and a negative pressure/gas outlet port;
    a wall defining a fluid-impermeable boundary between the exchange compartment and the dialysate degassing compartment;
    a first hollow fibre membrane formed from hollow hydrophilic fibres within the exchange compartment of the housing, where each of the fibres have an inner surface and an outer surface and where the inner surface of the hollow hydrophilic fibres are aligned co-axially with respect to the alignment of the blood inlet and outlet ports, and the outer surface of the hollow fibres is aligned perpendicularly with respect to the alignment of the first dialysate inlet and outlet ports; and
    a second hollow fibre membrane formed from hollow hydrophobic fibres within the dialysate degassing compartment of the housing, where each of the fibres have an inner surface and an outer surface, where the inner surface of the hollow fibres is aligned co-axially with respect to the alignment of the second dialysate inlet and outlet ports and the outer surface of the hollow fibres is aligned perpendicularly with respect to the alignment of the degassing gas inlet port and the negative pressure/gas outlet port, optionally wherein the device further comprises a device for regenerating dialysate.

24. A method of haemodialysis comprising the steps of treating a subject in need thereof with a haemodialysis device as described in any one of Clauses 20 to 23.

25. A method for controlling dialysate flow in a peritoneal dialysis system, the method comprising:
determining a number of outflow and/or inflow parameters of a dialysate from a subject flowing between a filter device and a sorbent device over one or more cycles, each cycle comprising an outflow phase and an inflow phase;
comparing the parameters against a set of predefined conditions for controlling the dialysate flow through the filter device comprising hydrophilic fibres;
apportioning, based on the comparison of the parameters, a regenerated dialysate to flow from the sorbent device to the filter device during the inflow phase; and
controlling a switching means or apparatus to send the apportioned regenerated dialysate to the hydrophilic fibres of the filter device.

26. The method according to Clause 25, wherein the parameters comprise an outflow rate of the dialysate passing through the filter device during the outflow phase of a current cycle, and the apportioned regenerated dialysate is sent to the filter device during the inflow phase of the current cycle.

27. The method according to Clause 26, wherein the parameters further comprise an outflow rate and/or an inflow rate of the dialysate passing through the filter device during the outflow phase and/or inflow phase, respectively, of a previous cycle.

28. The method according to Clause 27, wherein the parameters comprise the outflow rates during the outflow phases of the previous and current cycles, and the predefined conditions are associated with a difference between the outflow rates.

29. The method according to Clause 25, wherein the parameters comprise inflow rates of the dialysate passing through the filter device during the inflow phases of a current cycle and a previous cycle, the predefined conditions are associated with a difference between the inflow rates, and the apportioned regenerated dialysate is sent to the filter device during the inflow phase of a next cycle.

30. The method according to any one of Clauses 25 to 29, wherein the regenerated dialysate for one of the one or more cycles is apportioned based additionally on the apportioned regenerated dialysate for one or more previous cycles.

31. A kit of parts comprising:
  (a) a peritoneal dialysis filter device according to Clause 1; and
  (b) a post-filtration system, which comprises:
  a first fluid pathway;
  a second fluid pathway, which comprises a post-filtration sorbent compartment; and
  a switch for selecting between the first and second fluid pathways, where the first and second fluid pathways are both fluidly connected to the first port of the housing via the switch, where the sorbent compartment comprises a post-filtration sorbent that is suitable for removing one or more of water-soluble uremic toxins, protein-bound uremic toxins, low-molecular weight proteins, endotoxins, exotoxins, inflammatory mediators and microorganisms.

32. A kit of parts comprising:
  (i) a peritoneal dialysis filter device according to Clause 3; and
  (ii) a post-filtration system, which comprises:
    (a) a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or
    (b) a post-filtration sorbent placed within the headspace cavity portion, where said sorbent is suitable for removing one or more of water-soluble uremic toxins, protein-bound uremic toxins, low-molecular weight proteins, endotoxins, exotoxins, inflammatory mediators and microorganisms.

33. A kit of parts comprising:
  (i) a peritoneal dialysis filter device according to Clause 5; and
  (ii) a post-filtration system, which:
    (a) comprises a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) further comprises a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

DESCRIPTION

The current invention seeks to solve some or all of the problems identified hereinbefore by the use of a filter as described in more detail herein below.

Figure 1:
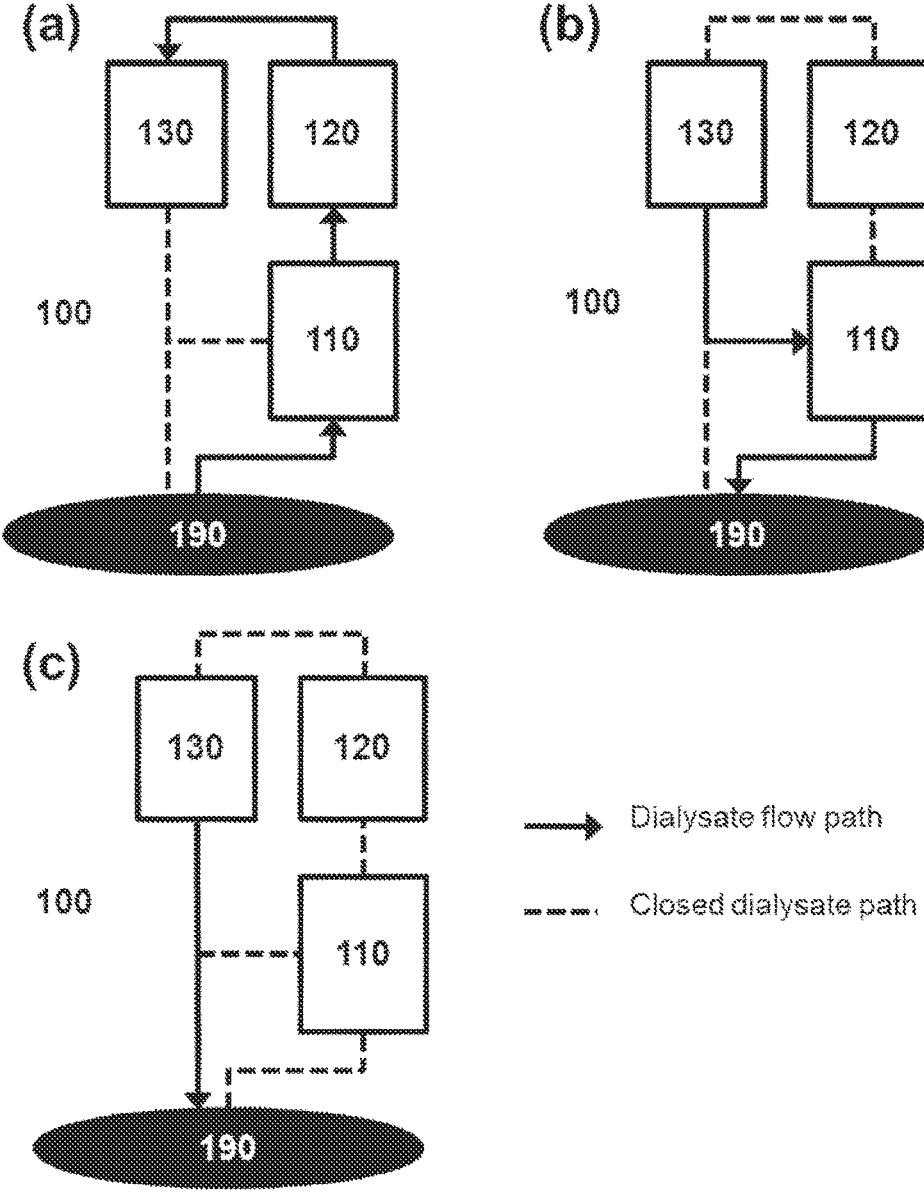
FIG. 1 Depicts a sorbent-based dialysis system 100 incorporating the advanced filter system 110 of the current invention in three different phases: (a) outflow; (b) inflow washback; and (c) inflow bypass.

In a sorbent-based dialysis system 100, the flow schematic and the key modules in the device can be presented as below (FIG. 1). The entire therapy comprises of a number of cycles of tidal dialysis. Each cycle starts from an outflow phase (FIG. 1*a*), during which fluid comes out from the patient 190 and passes through the advanced filtering system 110 before passing through a sorbent device 120 for detoxification and electrolyte control. The dialysate fluid accumulates in a reservoir chamber 130. After this outflow phase is completed, an inflow phase will kick off immediately, this consists of two phases (FIGS. 1*b* and *c*). The first phase is a washback inflow (FIG. 1*b*), where a portion of the regenerated dialysate is directed from the reservoir chamber 130 and through the advanced filtering system 110, and the second phase sees the remaining regenerated dialysate (the majority) directly flow back to the patient's peritoneum 190 from the reservoir chamber 130 without passing through the advanced filtering system 110 (i.e. a bypass inflow) (FIG. 1*c*). The washback phase is needed because proteins become trapped within the advanced filtering system over the course of the outflow phase 110 (e.g. in the walls of the hollow fibres, as will be described in more detail below).

A level sensor can be implemented to monitor how long it takes for fluid to accumulate inside the reservoir or leave the reservoir, or alternatively a volumetric flow rate sensor can serve the same purpose. This method can monitor the flow rate inside the system for that particular cycle for both the outflow and inflow phase.

A peritoneal dialysis system according to the current invention may comprise, a filter device;

a sorbent device, wherein the filter device is arranged to receive and filter the entirety of dialysate from a subject and to provide the filtered dialysate to a sorbent device when operated in an outflow direction; and the filter device is arranged to receive at least part of a regenerated dialysate from the sorbent device, which passes through the hydrophilic fibres of the filter device and back to the subject when operated in an inflow direction.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

When used herein, the term "sorbent device" may refer to any suitable such device that can be used in combination with any filter device as described herein. This may be a purpose-built sorbent device, but it may also refer to a retrofitted sorbent device that has been adapted to accommodate the filter devices disclosed herein. As will be appreciated, the sorbent device described herein requires the presence of the sorbent device 120 and reservoir chamber 130 mentioned hereinbefore, along with a suitable pumping means or apparatus (e.g. a gear pump, diaphragm pump, piston pump, hydraulic pump, pneumatic pump, peristaltic pump and mechanical pump).

Figure 2:
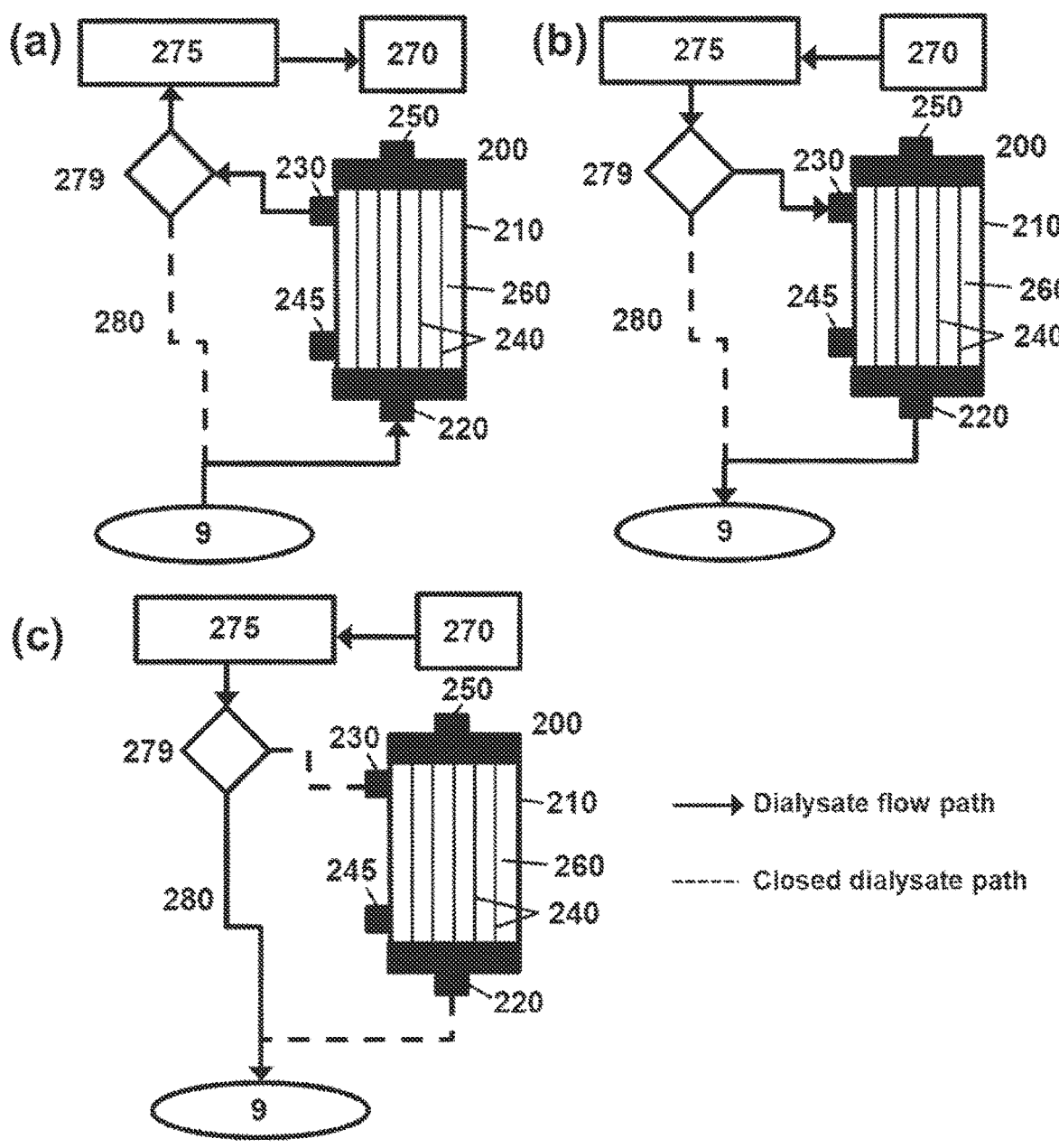
FIG. 2 Depicts a filter system incorporating the single-chamber filter device 200 of the current invention in three different phases: (a) outflow; (b) inflow washback; and (c) inflow bypass.

A first filter system that is disclosed herein that can be used in a peritoneal dialysis system is a dead-end filter, which can be used with any suitable peritoneal dialysis sorbent. FIGS. 2*a-c* shows such a filter system in a peritoneal dialysis device. This filter system is intended to prevent proteins & leukocytes from coming into contact with the sorbent during outflow. Thus, there is disclosed a peritoneal dialysis filter device 200, which comprises:

a housing 210 comprising a first port 220 and a second port 230; and a hollow fibre membrane 240 formed from hollow hydrophilic fibres within the housing 210, where each of the fibres have an inner surface and an outer surface, wherein the inner surface of the hollow hydrophilic fibres are aligned co-axially with respect to the alignment of the first port 220 and the outer surface of the hollow fibres is aligned perpendicularly with respect to the alignment of the second port 230, such that, when used:

a dialysate from a subject enters the filter device 200 through the first port 220 and exits via the second port 230 in an outflow direction; and a regenerated dialysate from the sorbent device enters the filter device 200 through the second port 230 and exits via the first port 220 in an inflow direction.

The ports described herein may be solely open or may be adjustable between an open setting and a closed setting, thereby providing more control over the flow of fluid.

While the system may operate without it, the embodiments described below also make use of a bypass means or apparatus. This may comprise:

a bypass fluid pathway connected to the sorbent device and arranged to return a regenerated dialysate to the subject without passing through the filter device; and a switching means or apparatus that selects between sending a regenerated dialysate to the filter device or to the bypass fluid pathway.

A "switching means or apparatus" may refer to any suitable apparatus that can open or close a means of fluid communication, or which may divert a fluid between one or more lines of fluid communication. Examples of suitable switching means an apparatus that may be mentioned herein include, but are not limited to a valve (e.g. a ball valve, a switch valve etc), a stopcock and a combination of a T-junction and switches. When the system does not include a bypass means or apparatus, the entirety of the regenerated dialysate may pass through the filter device.

The dead-end filter 200 can be used in a minimum 2-port configuration (i.e. first 220 and second 230 ports), but it may also be provided in a 3- or 4-port configuration (third port 245 and fourth port 250) can be used to improve priming of the entire device at the beginning of the therapy. During inflow phase, the flow can be directed back into the filter to washback the proteins and leukocytes to the patient. This can reduce protein loss that is typical in conventional peritoneal dialysis. This concept is not constrained by the particular filter shape, it can be circular, square, spiral, sheet form, etc.

In operation, the first step is an outflow phase (FIG. 2*a*) that may last for any suitable amount of time (e.g. 5 minutes) and involve the removal of fluid from a subject (e.g. 250 mL). In this first step, the first 220 and second 230 ports are set to open (if they can be opened and closed) and spent dialysate is pumped from the patient's peritoneum 9 through the first port 220 of the filter device 200 and so enters the inner surface of the hollow fibre membrane (as the first port is co-axially aligned with the hollow fibres), where it enters the inner channel of the hydrophilic hollow fibres 240. Due to negative pressure exerted on the exterior surface of the hollow fibres, water and low molecular weight solutes (e.g. <40 kDa—as will be appreciated, the molecular weight cut-off depends on the pore size of the filter and this may be varied by the skilled person to any suitable value) are transported from the inner channel of the hollow fibres 240, through the porous wall matrix, to the outer chamber 260 surrounding the exterior of the hollow fibres. As will be appreciated, positive pressure may be used instead to achieve the same effect. Larger solutes such as proteins and fibrin are trapped on the lumen surface of the hollow fibres 240, preventing their interaction with interior components of the purification system 270. The filtered spent dialysate is then pumped from the second port 230 of the filter device 200 by pump 275 to the purification system 270 via a switch 279. The filtered spent dialysate is then processed by the purification system 270 into regenerated fresh dialysate.

While 40 kDa is used above as the molecular cut-off for the filter, it will be understood that any suitable pore size for the filter may be used. For example, a suitable pore size for the filter that may be used in all embodiments disclosed herein may be a pore size that provides a molecular weight cut-off in the range of from 5 to 7 kDa.

When used herein, the term "co-axially aligned" is intended to mean that the axis of the first port is aligned with the directional axis of the lumen of the hollow fibres.

The regenerated fresh dialysate is then transported back to the subject's peritoneum by two means. In the first instance (FIG. 2*b*), the first 220 and second 230 ports are retained in the open setting (if they can be closed) and the regenerated fresh dialysate is transported from the purification system 270 by pump 275 to the second filter port 230 via switch 279. Downstream from purification system 270, the fresh dialysate encounters and mixes with spent dialysate from the previous outflow. The mixture of fresh and spent dialysate (the combination of which make up the washback fluid)

enters the filter chamber 260, exerting a positive fluidic pressure on the exterior surface of the hollow fibres 240. Due to this positive fluidic pressure, water and low molecular weight solutes such as glucose and electrolytes are forced through the porous wall matrix through to the inner channel of the hydrophilic fibres 240. During this process, any proteins or biological material trapped on the lumen of the fibres are dislodged, de-fouling the inner pores of the fibre and restoring the original filter surface area. Without wishing to be bound by theory, it is believed that the washback is more effective when done across the fibres as opposed to through the fibres. When washback is done through the fibres, there is practically no resistance to the fluid movement. The washback fluid exits the filter through port 220 and re-enters the peritoneum 9. The volume of washback fluid is optimised such that a minimum of spent fluid is returned to the patient, while ensuring patency of the filter is maintained for the next outflow cycle. As will be appreciated, only a small amount of the regenerated dialysate is required for the washback under normal circumstances. Thus, the amount of fluid used may be relatively small (e.g. 50 mL) and the time needed to complete the washback phase may be less than a minute.

As shown in FIG. 2*c*, the remaining regenerated fresh dialysate does not need to pass through the filter device 200 and is instead transported from the purification system 270 by pump 275 to the bypass line 280 via switch 279. In this circumstance, the first 220 and second 230 ports may be set to closed (if they have this setting). As will be appreciated, as the switch 279 may prevent fluid from flowing to the filter device 200 without the need for the ports to be switched from an open to a closed setting. Downstream from purification system 270, the fresh dialysate encounters and mixes with a small amount of washback fluid from the previous inflow washback cycle. Due to routing by switch 279, the predominantly fresh dialysate bypasses the chamber 260 and instead directly re-enters the peritoneum 9 via bypass line 280. The volume of inflow bypass fluid is optimised such that a maximum of fresh fluid is returned to the patient, in order to sustain a sufficient dialysate/serum gradient for efficient toxin removal and electrolyte control. For example, the inflow bypass fluid may be 200 mL (compared to 250 mL for the outflow). More generally:

Outflow: the device draws "T" liters of fluid from patient and de-toxifies it; and Inflow: the device puts back the "T" liters of "de-toxified" fluid back to patient, where:

washback: x % of fluid will be pushed back to patient; and bypass: 1-x % of fluid will be bypassed through the advanced filter and directly pushed back to patient.

The system above may be supplemented by a post-filtration system. Thus, the filter device may further comprise a post-filtration system, which comprises:

a first fluid pathway;

a second fluid pathway, which comprises a post-filtration sorbent compartment; and a switch for selecting between the first and second fluid pathways, where the first and second fluid pathways are both fluidly connected to the first port of the housing via the switch, where the sorbent compartment comprises a post-filtration sorbent that is suitable for removing one or more of water-soluble uremic toxins, protein-bound uremic toxins, low-molecular weight proteins, endotoxins, exotoxins, inflammatory mediators and microorganisms.

Figure 3:
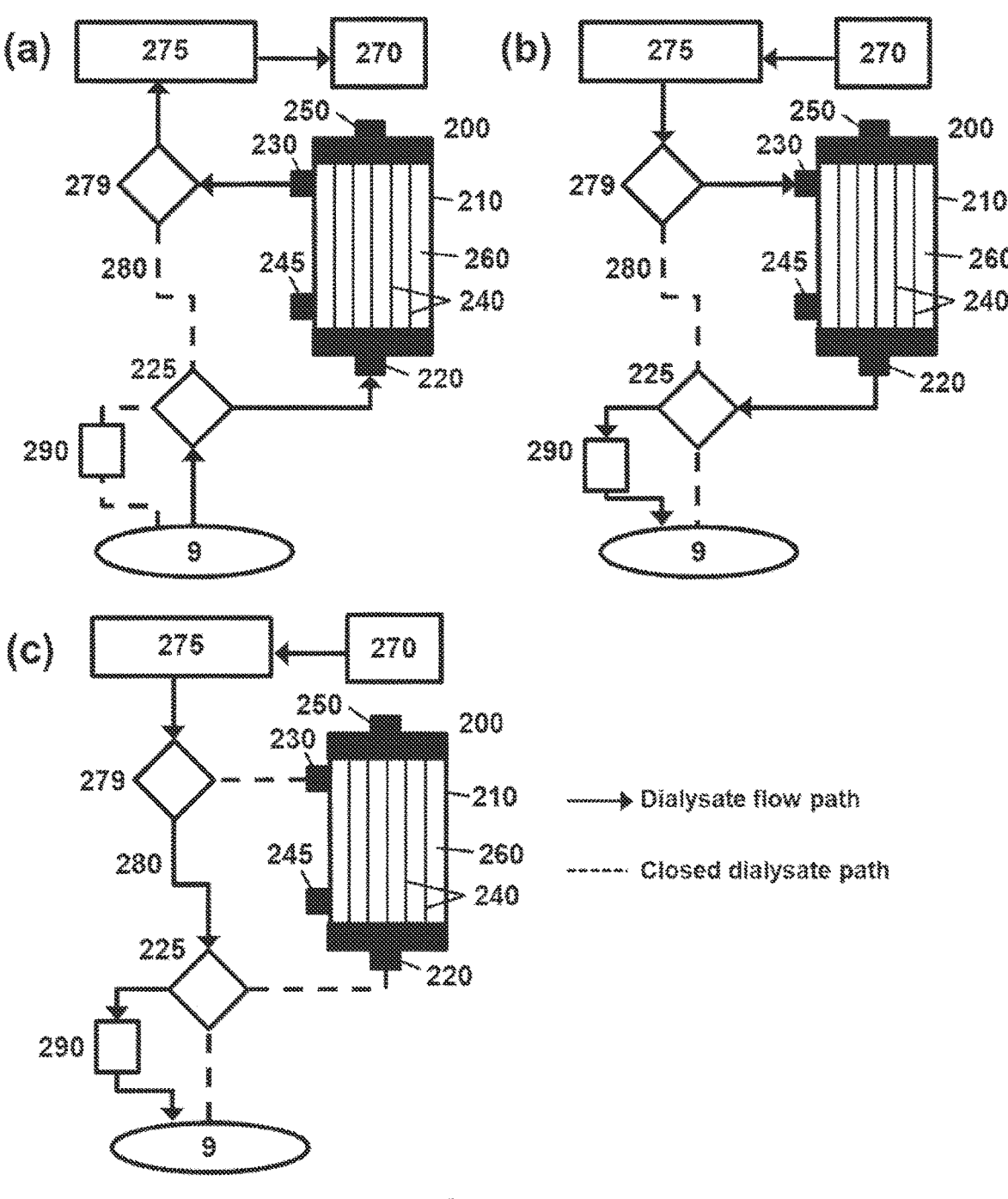
FIG. 3 Depicts a filter system incorporating the single-chamber filter device 200 of the current invention, with an activated carbon purification module and an additional switch, in three different phases: (a) outflow; (b) inflow washback; and (c) inflow bypass.

This arrangement will now be discussed with reference to FIGS. 3*a*-3*c*. The only difference between the first design and this design is the inclusion of an activated carbon purification module and a switch, with appropriate fluid pathways. It will be appreciated that the activated carbon purification compartment is an embodiment of the post-filtration sorbent compartment referred to above. Examples of other suitable materials for use in a post-filtration sorbent compartment are described below. For the avoidance of doubt, activated carbon may be used as an example in further embodiments below, but this is not intended to limit the designs to activated carbon—any other suitable material that can be used in a post-filtration system to achieve the goals described hereinbelow may be used instead.

The outflow operation (FIG. 3*a*) is essentially identical to that described before, but for the addition of switch 225, which is arranged to be in fluid communication with the first port 220 during outflow operation of the device. The main differences lie when the device is operated in the inflow direction.

Thus, in the first step of inflow operation (FIG. 3*b*), regenerated fresh dialysate is transported back to the subject's peritoneum 9 by two means. In the first instance, the regenerated fresh dialysate is transported from the purification system 270 by pump 275 to the second filter port 230 via switch 279. Downstream from purification system 270, the fresh dialysate encounters and mixes with spent dialysate from the previous outflow. The mixture of fresh and spent dialysate (the combination of which make up the washback fluid) enters the filter chamber 260, exerting a positive fluidic pressure on the exterior surface of the hollow fibres 240. Due to this positive fluidic pressure, low molecular weight solutes such as water, glucose and electrolytes are forced through the porous wall matrix through to the inner channel of the hydrophilic fibres 240. During this process, any proteins or biological material trapped on the lumen of the fibres are dislodged, de-fouling the inner pores of the fibre and restoring the original filter surface area. Without wishing to be bound by theory, it is believed that the washback is more effective when done across the fibres as opposed to through the fibres. When washback is done through the fibres, there is practically no resistance to the fluid movement. The washback fluid exits the filter through port 220 and is routed via switch 225 through compartment 290 where, for example, PBUTs and water soluble uremic toxins are removed by activated carbon. The treated washback fluid re-enters the peritoneum 9. The volume of washback fluid is optimised such that a minimum of spent fluid is returned to the patient, while ensuring patency of the filter is maintained for the next outflow cycle.

As shown in FIG. 3*c*, the regenerated fresh dialysate is transported from the purification system 270 by pump 275 to the bypass line 280 via switch 279. Downstream from purification system 270, the fresh dialysate encounters and mixes with a small amount of washback fluid from the previous inflow washback cycle. Due to routing by switch 279, the predominantly fresh dialysate bypasses the chamber 260 and instead enters bypass line 280. The predominantly fresh dialysate is then routed via switch 225 through compartment 290 where, for example, PBUTs and water soluble uremic toxins are removed by activated carbon. The predominantly fresh dialysate re-enters the peritoneum 9. As before, the volume of inflow bypass fluid is optimised such that a maximum of fresh fluid is returned to the patient, in order to sustain a sufficient dialysate/serum gradient for efficient toxin removal and electrolyte control.

In an alternative arrangement, second type of filter device may be used. This filter system 300 is a little more complex and comprises: a housing 310 comprising:

a first compartment 311 having a first port 312, and a second port 313;

a second compartment 315, having a third port 316, an inlet port 317 and an outlet port 318;

a switching means or apparatus 320 fluidly connected to the first 312 and third 316 ports;

a head-space cavity portion 330 that fluidly connects the first compartment 311 to the second compartment 315;

a first hollow fibre membrane 340 formed from hollow hydrophilic fibres within the first compartment 311 of the housing 310, where each of the fibres have an inner surface and an outer surface and where the inner surface of the hollow hydrophilic fibres are aligned co-axially with respect to the alignment of the first port 312 and the outer surface of the hollow fibres is aligned perpendicularly with respect to the alignment of the second port 313; and a second hollow fibre membrane 350 formed from hollow hydrophobic fibres within the second compartment 315 of the housing 310, where each of the fibres have an inner surface and an outer surface, where the inner surface of the hollow hydrophobic fibres are aligned co-axially with respect to the alignment of the third port 316 and the outer surface of the hollow fibres is aligned perpendicularly with respect to the alignment of the inlet 317 and/or outlet 318 ports, such that, when in use:

a dialysate from a subject enters the first compartment 311 of the filter device 300 through the first port 312 and exits the first compartment of the filter device via the second port 313 in an outflow direction; and a regenerated dialysate from the sorbent device enters the first compartment 311 of the filter device through the second port 313, passes through the head-space cavity 330 into the second compartment 315, where the hollow hydrophobic fibres degasses the regenerated dialysate before it exits through the third port 316, with the removed gas exiting the system via the outlet port 318.

When used herein, the term "degas" or "degasses" is intended to refer to the removal of unwanted gasses and/or bubbles from the regenerated dialysate, or other fluids, as the case may be. An example of an unwanted gas that may be removed is carbon dioxide. As will be appreciated, not all of the unwanted gasses may be removed from the regenerated dialysate by the process, but at least a portion of said gasses may be removed (e.g. from 10 to 99.99%). In certain embodiments, when seeking to remove unwanted gasses such as carbon dioxide, a sweep gas (e.g. air, oxygen, a mixture of oxygen and nitrogen or carbogen (95% oxygen and 5% $CO_2$)) may be used to replace the carbon dioxide in the regenerated dialysate. This sweep gas may be used alone, or in combination with negative pressure. In alternative embodiments, only negative pressure may be applied, which will therefore act to remove some or all of the gas and bubbles within the regenerated dialysate. As will be appreciated, the exact sweep gas used (and its flow rate) may depend on the application and may be determined by a skilled practitioner using their experience and knowledge. For example, if a subject has respiratory failure, then the skilled person may choose to use a flow rate and sweep gas recommended in the Extracorporeal Life Support Organization (ELSO) Guidelines for Adult Respiratory Failure, August, 2017.

As before, the system may be operated using a bypass means or apparatus, which will be discussed below. This bypass means or apparatus may have two possible configurations which may comprise:

(a) a bypass fluid pathway connected to the sorbent device and arranged to return a regenerated dialysate to the subject without passing through any part of the filter device; and a switching means or apparatus 360 that selects between sending a regenerated dialysate to the filter device or to the bypass fluid pathway; or (b) a bypass fluid pathway connected to the sorbent device and arranged to return a regenerated dialysate to the subject which passes through the second compartment of the filter device, which comprises a fourth port 319, such that the dialysate enters the second compartment 315 through the fourth port 319 and exits through the third port 316; and a switching means or apparatus 360 that selects between sending a regenerated dialysate to the second port or fourth port of the filter device.

Figure 4:
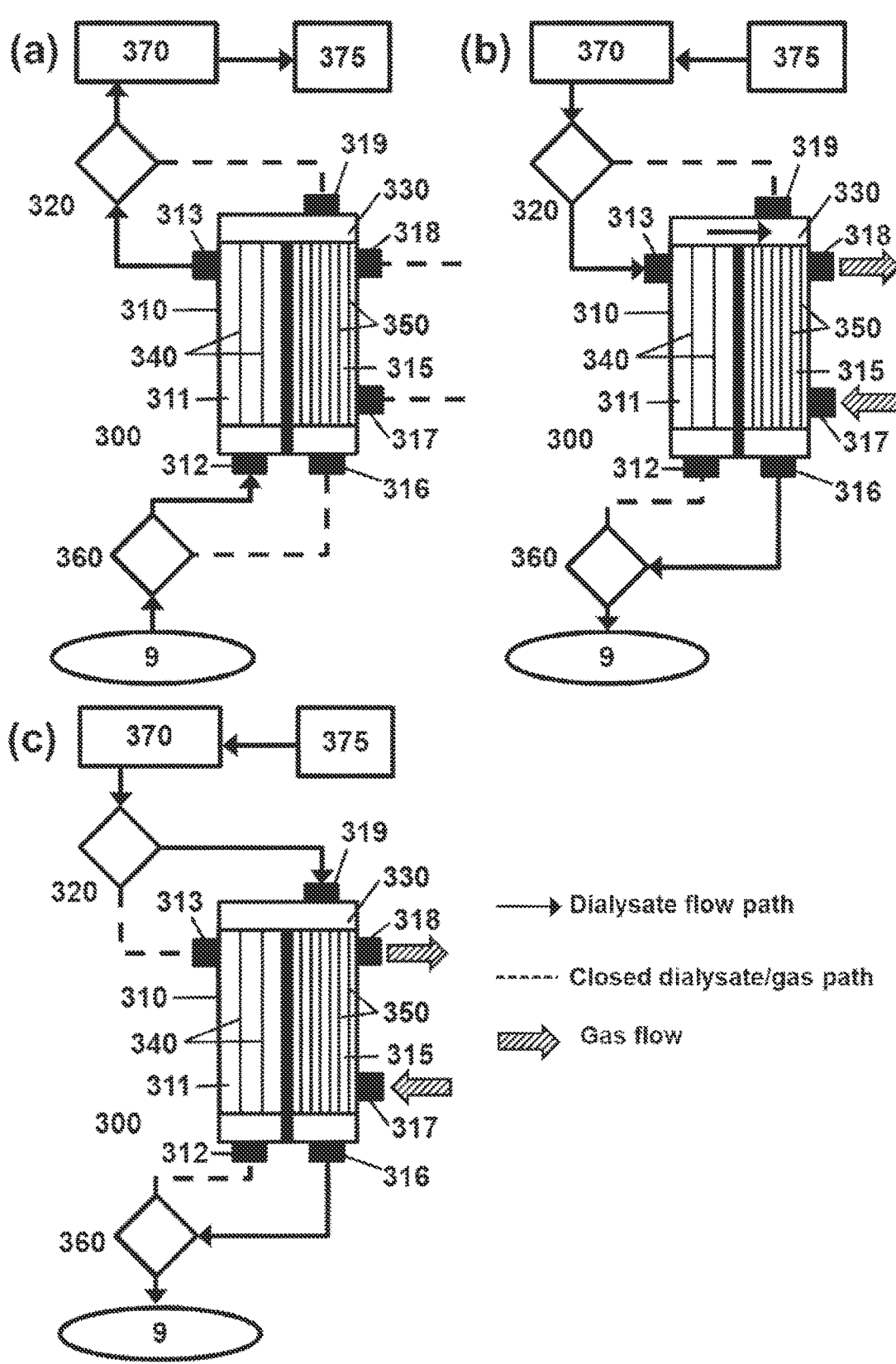
FIG. 4 Depicts a filter system incorporating the double-chamber filter device 300 of the current invention in three different phases: (a) outflow; (b) inflow washback; and (c) inflow bypass.

An embodiment of this arrangement is disclosed in FIGS. 4a to 4c.

In the outflow phase (FIG. 4a), spent dialysate is pumped from the patient's peritoneum 9 through the first port 312 of the hollow fibre membrane (via switch 360). Should the ports be capable of being opened and closed, the first and second ports are in the open position, while the other ports are in the closed position. The spent dialysate then enters the inner channel of the hydrophilic hollow fibres 340. Due to negative pressure exerted on the exterior surface of the hollow fibres, water and low molecular weight solutes (e.g. <40 kDa) are transported from the inner channel of the hollow fibres 340, through the porous wall matrix, to the first chamber 311 surrounding the exterior of the hollow fibres. Larger solutes such as proteins and fibrin are trapped on the lumen surface of the hollow fibres, preventing their interaction with interior components of the purification system 375. The filtered spent dialysate is then pumped from the second port 313 of the hollow fibre membrane by pump 370 to the purification system 375 via switch 320. The filtered spent dialysate is then processed by the purification system 375 into regenerated fresh dialysate.

In the first part of the inflow phase (FIG. 4b), the regenerated fresh dialysate is transported from the purification system 375 by pump 370 to the second filter port 313 via switch 320. Downstream from purification system 375, the fresh dialysate encounters and mixes with spent dialysate from the previous outflow. The mixture of fresh and spent dialysate (the combination of which make up the washback fluid) enters the first filter chamber 311, exerting a positive fluidic pressure on the exterior surface of the hollow fibres 340. Due to this positive fluidic pressure, water and low molecular weight solutes such as glucose and electrolytes are forced through the porous wall matrix through to the inner channel of the hydrophilic fibres 340. During this process, any proteins or biological material trapped on the lumen of the fibres are dislodged, de-fouling the inner pores of the fibre and restoring the original filter surface area. The washback fluid is routed through the headspace 330 of the hollow fibre and into the inner channel of the hydrophobic fibres 350 housed in the second chamber 315. The washback fluid may be degassed through use of a sweep gas though port 317 or a negative pressure applied through port 318, or a combination of both. The degassed washback fluid is purged from the filter through port 316 and re-enters the peritoneum 9 via switch 360. The volume of washback fluid is optimised such that a minimum of spent fluid is returned to the patient, while ensuring patency of the filter is maintained for the next outflow cycle. Should the ports be capable of being opened and closed, the second, third, outlet and fourth ports are in the open position, while the other ports are in the closed position.

The remaining regenerated fresh dialysate can bypass the first chamber as shown in FIG. 4*c*. Should the ports be capable of being opened and closed, the third, inlet, outlet and fourth ports are in the open position, while the other ports are in the closed position. In this embodiment, the remaining regenerated fresh dialysate is transported from the purification system 375 by pump 370 to the fourth filter port 319 via switch 320. Due to routing by switch 320, the fluid bypasses the first chamber 311 and instead enters the inner channel of the hydrophobic fibres 350, which are enclosed in the second chamber 315. Downstream from purification system 375, the fresh dialysate encounters and mixes with a small amount of washback fluid from the previous inflow washback cycle. The predominantly fresh dialysate enters inner channel of the hydrophobic fibres 350, is degassed via the mechanism and ports mentions previously (gas, negative pressure or combination of both via 317/318). The degassed predominantly fresh dialysate is pumped through filter outlet port 316 and re-enters the peritoneum 9 via switch 360. The volume of inflow bypass fluid is optimised such that a maximum of fresh fluid is returned to the patient, in order to sustain a sufficient dialysate/serum gradient for efficient toxin removal and electrolyte control.

The system may also comprise a post-filtration system, which may comprise:

(a) a fluid pathway situated between the third port of the housing and the switching means or apparatus, which fluid pathway comprises a post-filtration sorbent compartment, where the post-filtration sorbent compartment comprises a sorbent that is suitable for removing one or more of water-soluble uremic toxins, protein-bound uremic toxins, low-molecular weight proteins, endotoxins, exotoxins, inflammatory mediators and microorganisms; and/or (b) further comprises a post-filtration sorbent placed within the head-space cavity portion, where said sorbent is suitable for removing one or more of water-soluble uremic toxins, protein-bound uremic toxins, low-molecular weight proteins, endotoxins, exotoxins, inflammatory mediators and microorganisms.

In all embodiments of the invention that contain some sort of post-filtration sorbent system, the post-filtration sorbent may be any suitable sorbent that can remove one or more of water-soluble uremic toxins, protein-bound uremic toxins, low-molecular weight proteins, endotoxins, exotoxins, inflammatory mediators and microorganisms. Suitable sorbents for this role include those disclosed in Ronco C, Dell'Aquila R, Rodighiero MP (eds): Peritoneal Dialysis: A Clinical Update. Contrib Nephrol. Basel, Karger, 2006, vol 150, pp 336-343, which is incorporated herein by reference—particularly Table 1 of said document. Particular examples of sorbents that may be mentioned herein include, but are not limited to, activated carbon and macroporous polymeric materials.

Figure 5:
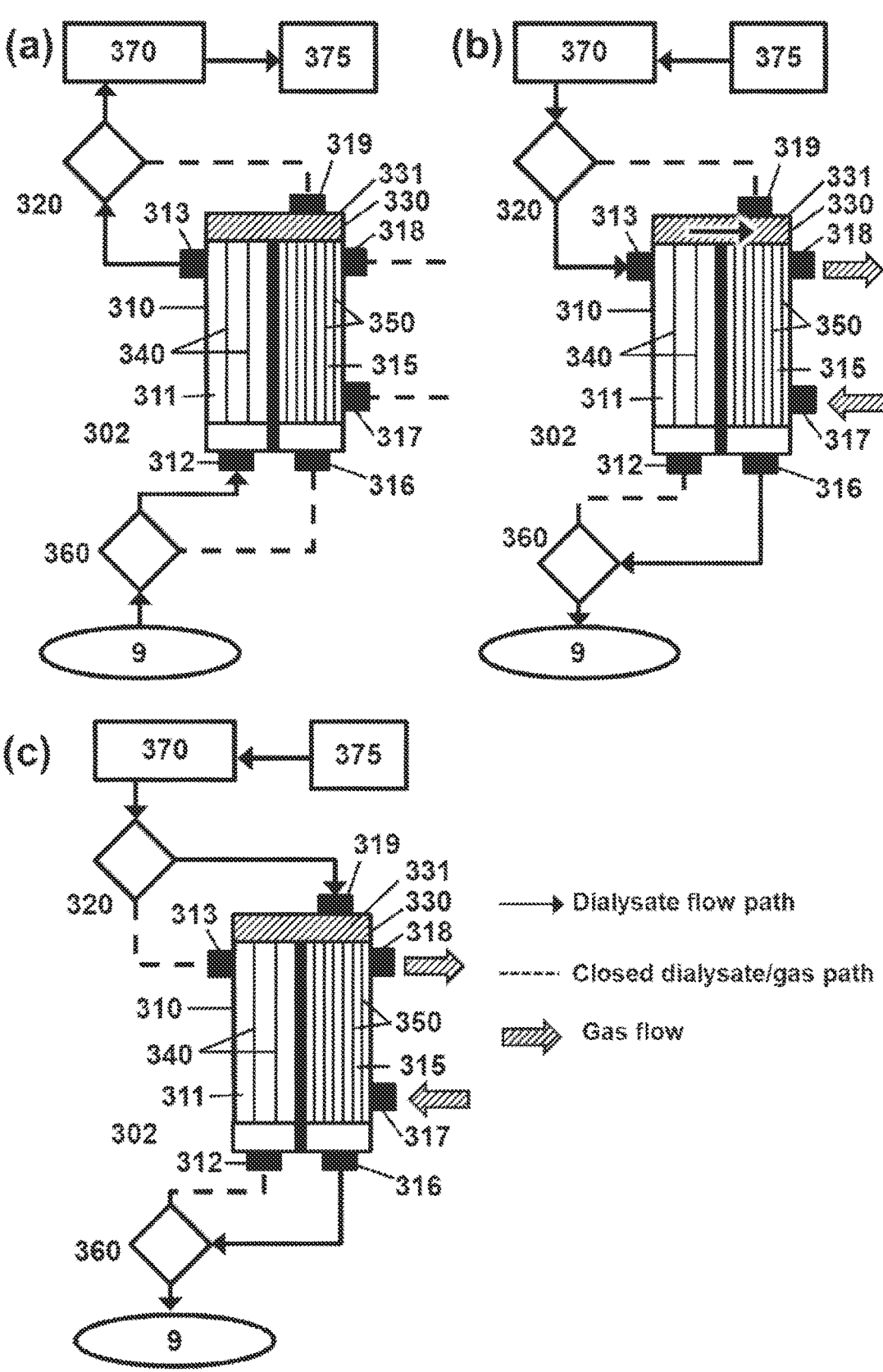
FIG. 5 Depicts a filter system incorporating the double-chamber filter device 302 of the current invention, with an activated carbon 331 placed within the head-space cavity portion 330, in three different phases: (a) outflow; (b) inflow washback; and (c) inflow bypass.

An embodiment of the latter (filter device 302) is disclosed in FIGS. 5*a* to 5*c*. There is no difference in the outflow operation, which can be understood by the above description for FIG. 4*a* and so is omitted here for brevity.

In the first part of the inflow phase (FIG. 5*b*), the regenerated fresh dialysate is transported from the purification system 375 by pump 370 to the second filter port 313 via switch 320. Downstream from purification system 375, the fresh dialysate encounters and mixes with spent dialysate from the previous outflow. The mixture of fresh and spent dialysate (the combination of which make up the washback fluid) enters the first filter chamber 311, exerting a positive fluidic pressure on the exterior surface of the hollow fibres 340. Due to this positive fluidic pressure, water and low molecular weight solutes glucose and electrolytes are forced through the porous wall matrix through to the inner channel of the hydrophilic fibres 340. During this process, any proteins or biological material trapped on the lumen of the fibres are dislodged, de-fouling the inner pores of the fibre and restoring the original filter surface area. The washback fluid is routed through the headspace compartment 330 where PBUTs and water soluble uremic toxins are removed by a sorbent 331 such as activated carbon, whereafter the fluid enters the inner channels of the hydrophobic fibres 350 housed in the second chamber 315. The washback fluid may be degassed through use of a sweep gas though port 317 or negative pressure can be applied through port 318, or a combination of both. The degassed washback fluid is purged from the filter through port 316 and re-enters the peritoneum 9 via switch 360. The volume of washback fluid is optimised such that a minimum of spent fluid is returned to the patient, while ensuring patency of the filter is maintained for the next outflow cycle. Should the ports be capable of being opened and closed, the second, third, outlet and fourth ports are in the open position, while the other ports are in the closed position.

The remaining regenerated fresh dialysate can bypass the first chamber as shown in FIG. 5*c*. Should the ports be capable of being opened and closed, the third, inlet, outlet and fourth ports are in the open position, while the other ports are in the closed position. In this embodiment, the remaining regenerated fresh dialysate is transported from the purification system 375 by pump 370 to the fourth filter port 319 via switch 320. Due to routing by switch 320, the fluid bypasses the first chamber 311 and instead enters the inner channel of the hydrophobic fibres 350, which are enclosed in the second chamber 315. Downstream from purification system 375, the fresh dialysate encounters and mixes with a small amount of washback fluid from the previous inflow washback cycle. Upon passing through filter port 319, the dialysate enters headspace compartment 330 where PBUTs and water soluble uremic toxins are removed by a sorbent such as activated carbon. Thereafter, the dialysate enters the inner channel of the hydrophobic fibres 350, which are enclosed in the second chamber 315, and may be degassed via the mechanism and ports mentions previously (gas, negative pressure or combination of both via 317/318). The degassed predominantly fresh dialysate is pumped through filter outlet port 316 and re-enters the peritoneum 9 via switch 360. The volume of inflow bypass fluid is optimised such that a maximum of fresh fluid is returned to the patient, in order to sustain a sufficient dialysate/serum gradient for efficient toxin removal and electrolyte control.

Figure 6:
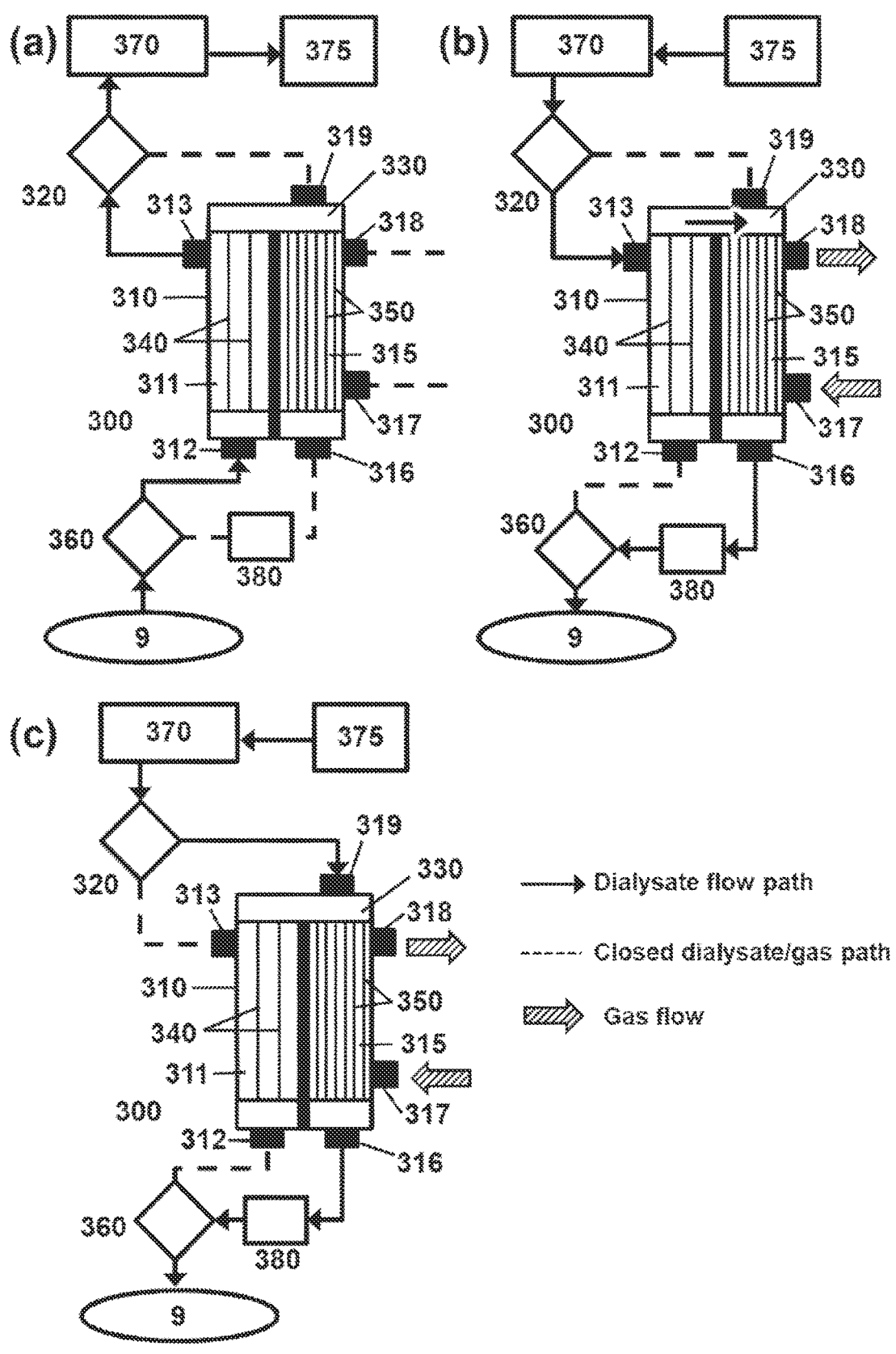
FIG. 6 Depicts a filter system incorporating the double-chamber filter device 300 of the current invention, with an activated carbon compartment 380, in three different phases: (a) outflow; (b) inflow washback; and (c) inflow bypass.

As mentioned above, the system described above may operate using a filter device that uses an external activated carbon compartment. This is described in FIGS. 6*a* to 6*c*. Again, it will be understood that this external activated carbon compartment is equivalent to the external post-filtration sorbent compartment discussed hereinbefore.

The operation of FIG. 6*a* is essentially identical to that described by reference to FIG. 4*a* and so will be omitted here for brevity.

In the first part of the inflow phase (FIG. 6*b*), the regenerated fresh dialysate is transported from the purification system 375 by pump 370 to the second filter port 313 via switch 320. Downstream from purification system 375, the fresh dialysate encounters and mixes with spent dialysate from the previous outflow. The mixture of fresh and spent dialysate (the combination of which make up the washback fluid) enters the first filter chamber 311, exerting a positive fluidic pressure on the exterior surface of the hollow fibres 340. Due to this positive fluidic pressure, water and low molecular weight solutes such as glucose and electrolytes are forced through the porous wall matrix through to the inner channel of the hydrophilic fibres 340. During this process, any proteins or biological material trapped on the lumen of the fibres are dislodged, de-fouling the inner pores of the fibre and restoring the original filter surface area. The washback fluid is routed through the headspace 330 of the hollow fibre and into the inner channel of the hydrophobic fibres 350 housed in the second chamber 315. The washback fluid may be degassed through use of a sweep gas though port 317 or negative pressure can be applied through port 318, or a combination of both. The degassed washback fluid exits the filter through port 316 and is pumped through compartment 380 where PBUTs and water soluble uremic toxins are removed by activated carbon. The purified wash-back fluid re-enters the peritoneum 9 via switch 360. The volume of washback fluid is optimised such that a minimum of spent fluid is returned to the patient, while ensuring patency of the filter is maintained for the next outflow cycle. Should the ports be capable of being opened and closed, the second, third, outlet and fourth ports are in the open position, while the other ports are in the closed position.

The remaining regenerated fresh dialysate can bypass the first chamber as shown in FIG. 6c. Should the ports be capable of being opened and closed, the third, inlet, outlet and fourth ports are in the open position, while the other ports are in the closed position. In this embodiment, the remaining regenerated fresh dialysate is transported from the purification system 375 by pump 370 to the fourth filter port 319 via switch 320. Due to routing by switch 320, the fluid bypasses the first chamber 311 and instead enters the inner channel of the hydrophobic fibres 350, which are enclosed in the second chamber 315. Downstream from purification system 375, the fresh dialysate encounters and mixes with a small amount of washback fluid from the previous inflow washback cycle. The predominantly fresh dialysate enters inner channel of the hydrophobic fibres 350, is degassed via the mechanism and ports mentions previously (gas, negative pressure or combination of both via 317/318).

The degassed predominantly fresh dialysate is pumped through filter outlet port 316 and is pumped through compartment 380 where PBUTs and water soluble uremic toxins are removed by activated carbon. The predominantly fresh dialysate re-enters the peritoneum 9 via switch 360. The volume of inflow bypass fluid is optimised such that a maximum of fresh fluid is returned to the patient, in order to sustain a sufficient dialysate/serum gradient for efficient toxin removal and electrolyte control. The positioning of compartment 380 is advantageous as it allows for removal of both PBUTs from the washback fluid and of uremic toxins from the returned dialysate simultaneously, which would not be possible if the activated carbon was located in the purifier system 375.

In order for the filter devices of the current invention to function optimally, the filter system needs to be primed to remove trapped air from the system. The priming steps are listed as follows with reference to the configuration in FIGS. 6a-c.

1) A fill bag (in place of peritoneum 9) containing fresh dialysate is connected to switch 360.
2) Ports 316, 317, 318 and 319 are in closed position, while ports 312 and 313 are open. Switch 360 and 320 are routed, such that the fill bag is in fluid communication with port 312, and port 313 is in fluid communication with pump 370.
3) Pump 370 is switched on to prime the hydrophilic filters 340 by filling the internal lumen of the fibres, the external chamber 311, and exit port 313 with the dialysate.
4) Once priming of the hydrophilic fibres 340 is completed, pump 370 is switched off. Switch 360 is then routed to connect the fill bag to port 316, while switch 320 is routed to connect pump 370 to port 319.
5) Ports 317 and 318 are kept in the closed position.
6) Pump 370 is switched on to prime the lumen of the hydrophobic fibres 350.
7) Priming is complete and the fill bag is removed. The device can be connected to a patient for use. There may be some unprimed areas in the headspace 330, but this can be resolved in the subsequent inflow wash-back, which will push the air in the headspace 330 to the hydrophobic fibres 350 to be removed.

While the priming process allows the filter system to perform at its best, priming is optional and is not absolutely necessary in order for the filter device to function (and hence the dialysis system). The steps described above may be applied by analogy to prime any of the double-chamber filter devices disclosed herein. In addition, steps 1-3 and 7 may also be used to prime the single-chamber filters described herein.

In an alternative arrangement, second type of filter device may be used. This filter system 400 is a little more complex and comprises: a housing 410 comprising:

a first compartment 411 having a first port 412, and a second port 413;

a second compartment 415, having a third port 416, a fourth port 419, an inlet port 417 and an outlet port 418;

a switching means or apparatus 460 fluidly connected to the first 412 and third 416 ports;

a first hollow fibre membrane 440 formed from hollow hydrophilic fibres within the first compartment 411 of the housing 410, where each of the fibres have an inner surface and an outer surface and where the inner surface of the hollow hydrophilic fibres are aligned co-axially with respect to the alignment of the first port 412 and the outer surface of the hollow fibres is aligned perpendicularly with respect to the alignment of the second port 413; and a second hollow fibre membrane 450 formed from hollow hydrophobic fibres within the second compartment 415 of the housing 410, where each of the fibres have an inner surface and an outer surface, where the inner surface of the hollow hydrophobic fibres are aligned co-axially with respect to the alignment of the third 416 and fourth 419 ports and the outer surface of the hollow fibres is aligned perpendicularly with respect to the alignment of the inlet 417 and/or outlet 418 ports.

As mentioned before, the system may be operated using a bypass means or apparatus, which will be discussed below. This bypass means or apparatus may have two possible configurations which may comprise:

(a) a bypass fluid pathway connected to the sorbent device and arranged to return a regenerated dialysate to the subject without passing through any part of the filter device; and a switching means or apparatus 420 that selects between sending a regenerated dialysate to the filter device or to the bypass fluid pathway; or (b) a bypass fluid pathway connected to the sorbent device and arranged to return a regenerated dialysate to the subject which passes through the second compartment 415 of the filter device, such that the dialysate enters the second compartment 415 through the fourth port 419 and exits through the third port 416; and a switching means or apparatus 420 that selects between sending a regenerated dialysate to the second port 413 or fourth port 419 of the filter device.

Figure 7:
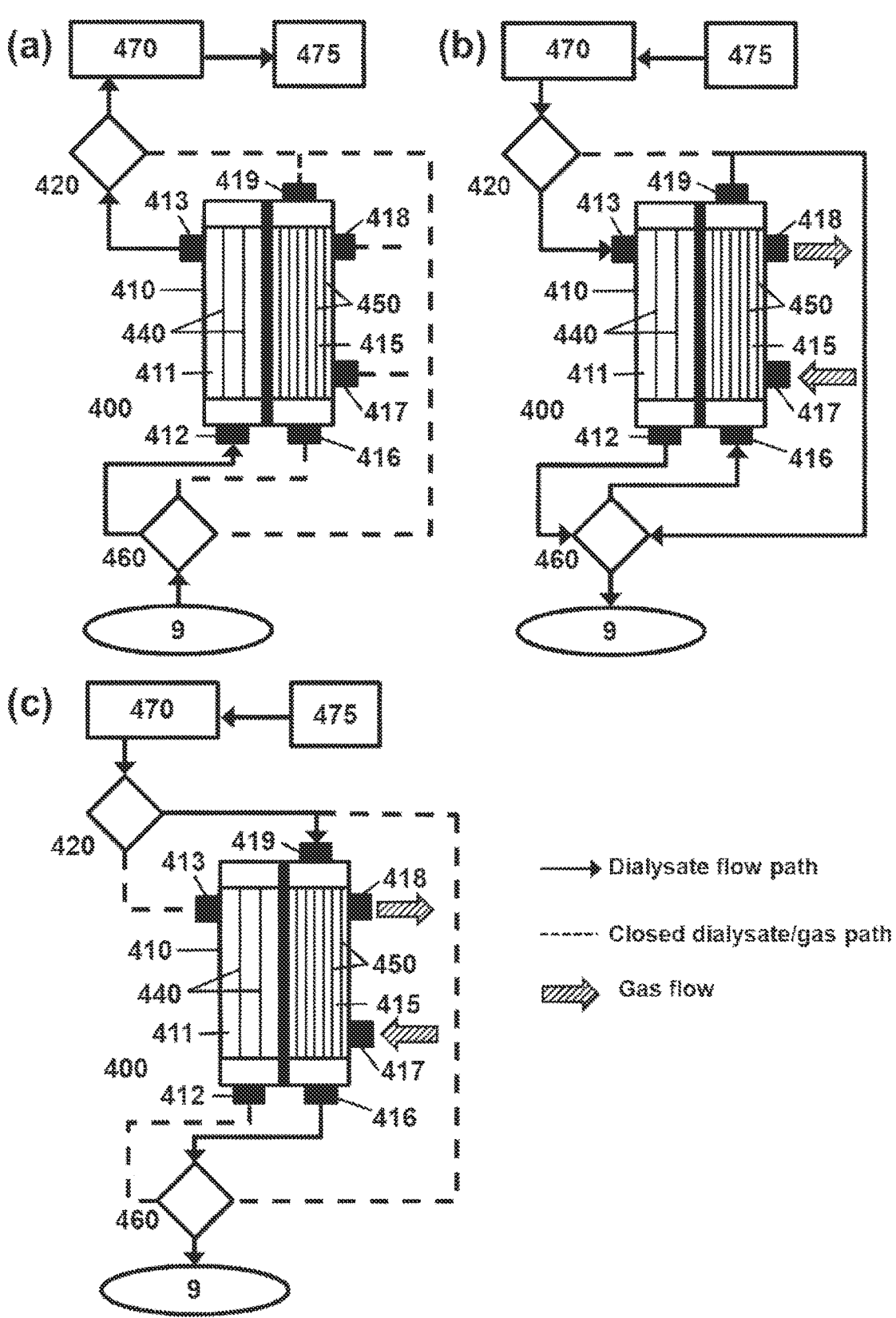
FIG. 7 Depicts a filter system incorporating the double-chamber filter device 400 of the current invention, with a bypass fluid pathway and a three-way switch 460, in three different phases: (a) outflow; (b) inflow washback; and (c) inflow bypass.

An embodiment of this arrangement is disclosed in FIGS. 7a to 7c.

The outflow operation of the device (FIG. 7a) is essentially identical to that described for FIG. 4a and so this will not be described again for brevity.

The first stage of the inflow mode is described in FIG. 7b, where all ports are in the open position (should they have the ability to be opened or closed). The regenerated fresh dialysate is transported from the purification system 475 by pump 470 to the second filter port 413 via switch 420. Downstream from purification system 475, the fresh dialysate encounters and mixes with spent dialysate from the previous outflow. The mixture of fresh and spent dialysate (the combination of which make up the washback fluid) enters the first filter chamber 411, exerting a positive fluidic pressure on the exterior surface of the hollow fibres 440. Due to this positive fluidic pressure, low molecular weight solutes such as water, glucose and electrolytes are forced through the porous wall matrix through to the inner channel of the hydrophilic fibres 440. During this process, any proteins or biological material trapped on the lumen of the fibres are dislodged, de-fouling the inner pores of the fibre and restoring the original filter surface area. The washback fluid exits through the port 412 and is directed via a three-way switch 460 to the inlet port 416 of the second chamber 415. The fluid enters inner channels of the hydrophobic fibres and may be degassed through use of a sweep gas though port 417 or negative pressure can be applied through port 418, or a combination of both. The degassed washback fluid is purged from the filter through port 419 and re-enters the peritoneum 9 via switch 460. The volume of washback fluid is optimised such that a minimum of spent fluid is returned to the patient, while ensuring patency of the filter is maintained for the next outflow cycle.

As shown in FIG. 7c, the remaining regenerated fresh dialysate is transported from the purification system 475 by pump 470 to the fourth filter port 419 via switch 420. Due to routing by switch 420, the fluid bypasses the first chamber 411 and instead enters the inner channel of the hydrophobic fibres 450, which are enclosed in the second chamber 415. Downstream from purification system 475, the fresh dialysate encounters and mixes with a small amount of washback fluid from the previous inflow washback cycle. The predominantly fresh dialysate enters inner channel of the hydrophobic fibres 450, is degassed via the mechanism and ports mentions previously (gas, negative pressure or combination of both via 417/418). The degassed predominantly fresh dialysate is pumped through filter outlet port 416 and re-enters the peritoneum 9 via switch 460. The volume of inflow bypass fluid is optimised such that a maximum of fresh fluid is returned to the patient, in order to sustain a sufficient dialysate/serum gradient for efficient toxin removal and electrolyte control. In this mode, ports 412 and 413 are closed, while the other ports are open (should they have the ability to be closed).

Figure 17:
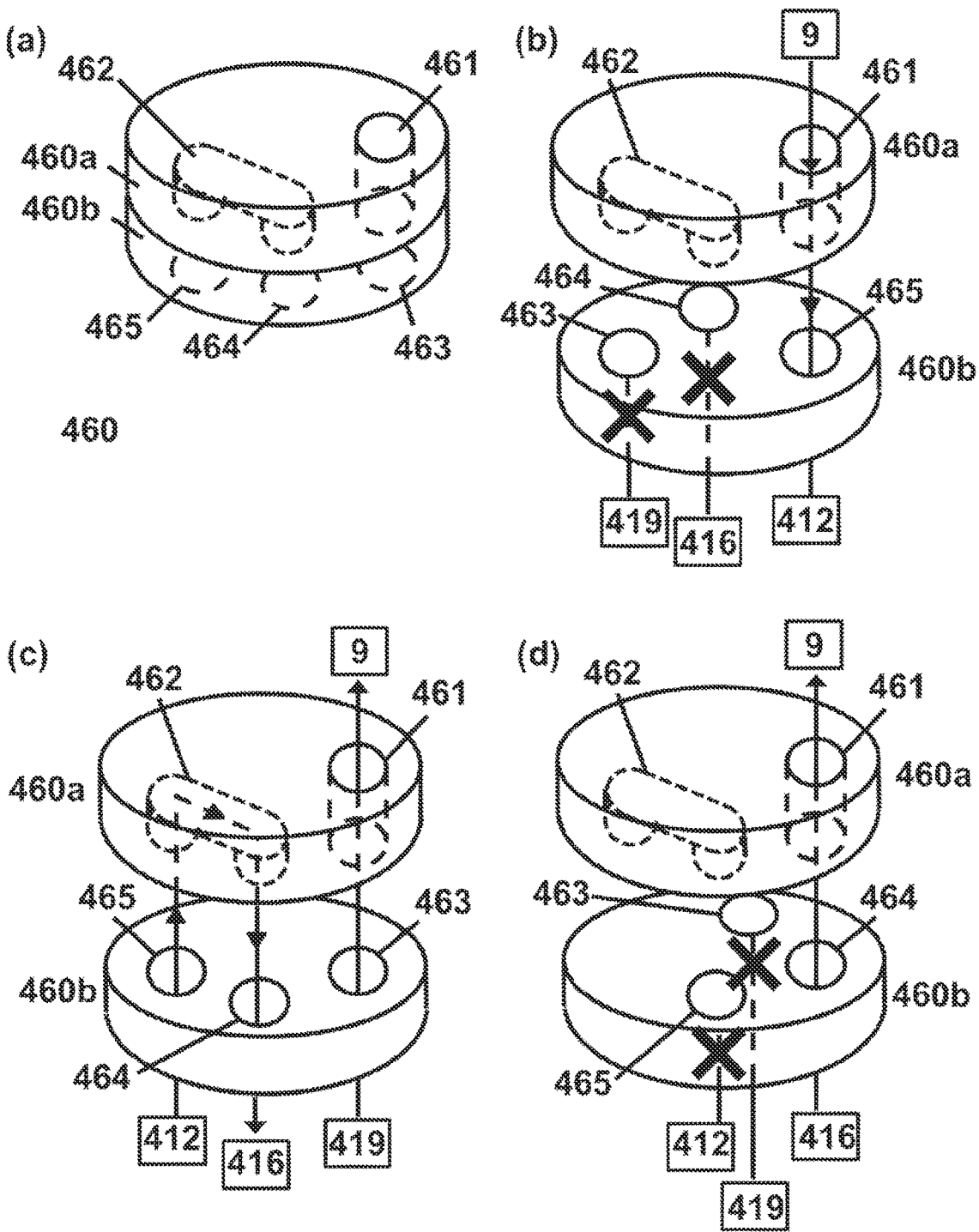
FIG. 17 Depicts the three-way manifold 460 for creating a three-way flow pattern as depicted in FIG. 7: (a) manifold parts 460*a* and 460*b* connected together; (b-d) positions of 460*a* and 460*b* in outflow, inflow washback and inflow bypass modes, respectively.

As will be appreciated, the three-way switch 460 in FIGS. 7a-c may be a manifold that connects to four different outlets/inlets and allows multiple flow pathways to be provided (as shown in FIGS. 17a-d). The manifold comprises two separate parts (460a and 460b) that can rotate relative to each other, and the two parts combine to create a leak-tight fitting (FIG. 17a).

Manifold part 460b has three through holes (463, 464 and 465), with a side (bottom of 460b) fluidly connected to outlets/inlets ports 419, 416 and 412, respectively, of device 400. Manifold part 460a contains one through hole 461 with a side (top) in fluid communication with peritoneum 9, and one internal conduit 462 with openings that can be aligned to two of the holes (464 and 465) in the corresponding part 460b to allow fluid communication between the ports.

As will be appreciated, the direction of dialysate flow is controlled by the alignment of the through holes (463, 464 and 465) of part 460b, with the openings of the internal conduit 462 and through hole 461 of part 460a. One or both of the manifold parts 460a and 460b may be rotated to facilitate the alignment of the through holes and openings of the internal conduit 462. In other words, one of the manifold parts may be fixed, while the other is active, or both parts may be active.

In the outflow mode, parts 460a and 460b are in a position as shown in FIG. 17b, whereby through holes 461 and 465 are aligned, which allows the flow of the dialysate from peritoneum 9 to inlet port 412 of device 400. However, through holes 463 and 464 are not aligned with conduit 462, and this closes the flow path between ports 419 and 416.

In the inflow washback mode (FIG. 17c), through holes 461 and 463 are aligned, which allows the flow of the dialysate from outlet port 419 to peritoneum 9. Further, through holes 464 and 465 are aligned with conduit 462, which therefore allows the flow of dialysate from ports 412 to 416.

In the inflow bypass mode (FIG. 17d), through holes 461 and 464 are aligned, therefore allowing the flow of the dialysate from outlet port 416 to peritoneum 9. However, through holes 463 and 465 are not aligned with the openings of conduit 462, and this closes the flow path between ports 412 and 419.

It will be appreciated that the system described above can be adapted to include a post-filtration system in the manner previously described.

As will be understood, the filter device described herein can be used with any suitable peritoneal dialysis system. This may be a system that has been purpose-built to incorporate the device or it may be a device that has been adapted to incorporate the device. As an example of this, we will now describe how one can retrofit the filter device of US Patent Application Publication Number 2018/0147338 A1, which is incorporated in its entirety herein by reference. One embodiment of this dialysis device is shown in FIG. 8 of the current application.

Figure 8:
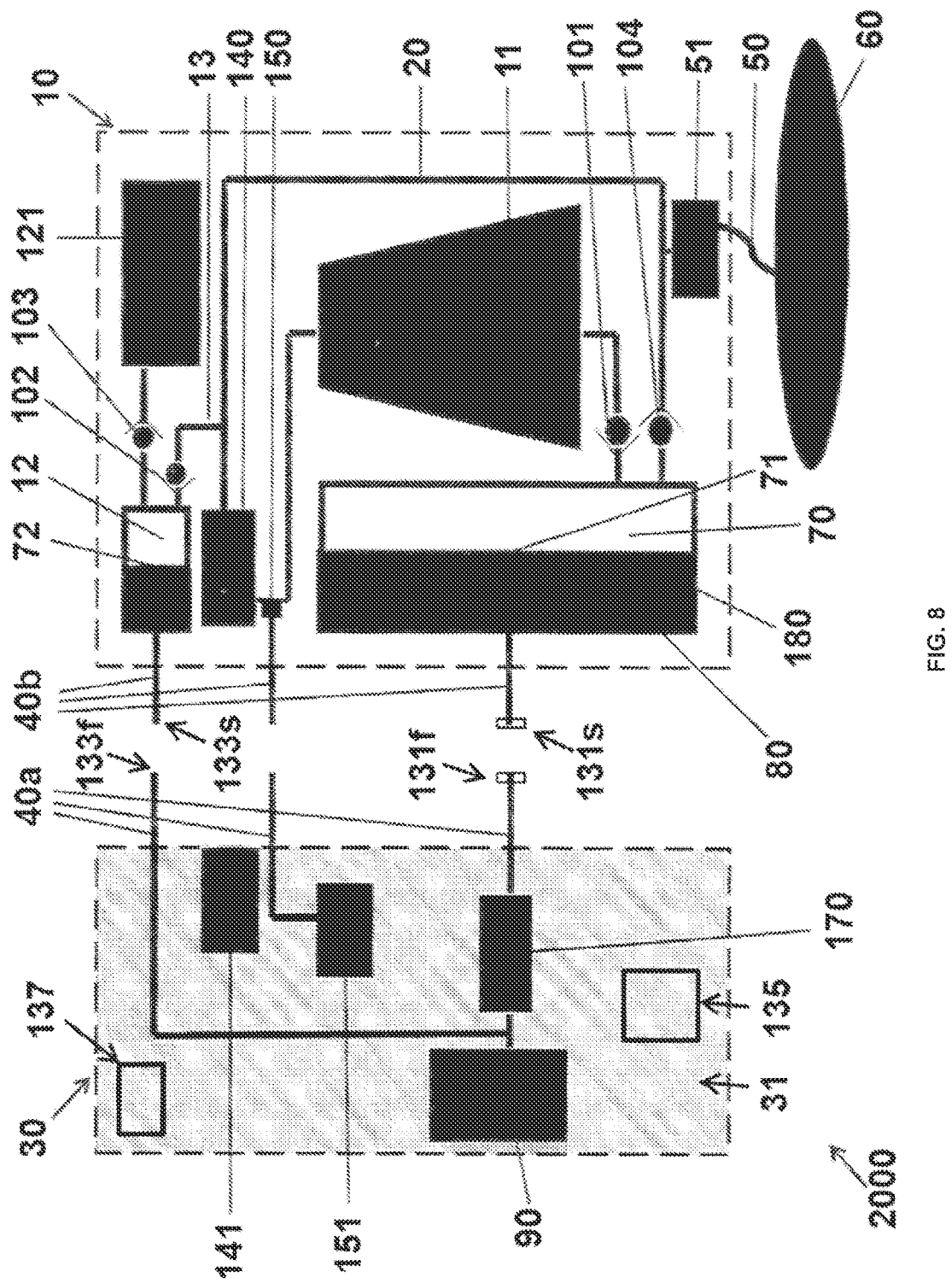
FIG. 8 Depicts a peritoneal dialysis device 2000, from US Patent Application Publication Number 2018/0147338 A1, which can be used with the filter device of the current invention.

In FIG. 8, the dialysis device (2000) comprises a disposable housing (10) having a flow path in the form of conduit (20), a controller (31) in the form of a control housing (30) for controlling the operation of the disposable housing (10). The dialysis device is powered by a battery (137). In this figure the disposable housing (10) and control housing (30) are not operably connected to each other. The disposable housing (10) and control housing (30) comprise interface in the form of a conduit connector (40a) disposed on said control housing (30) and (40b) disposed on the disposable housing (10) capable of connecting the control housing and the disposable housing. The disposable housing (10) and control housing (30) are brought into operative engagement when the conduit connector (40a) is brought into locking engagement with conduit connector (40b) The conduit (20)

of the disposable housing (10) is fluidly sealed from the control housing (30) and conduit connector (40a,40b).

The dialysis device comprises a flexible dialysate tube (50) which is capable of being in fluid communication with the peritoneum (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80). When the disposable housing (10) and control housing (30) are operably coupled to each other, the conduit connector (40a,40b) fluidly couples the pressure chamber (80) of the disposable housing (10) to a pump (90) located in the control housing (30). The conduit connector (40a,40b) comprises a first mating part (131f) and a second mating part (131s).

The pump (90) is configured to actuate the deformable diaphragm (71), by inducing a pressure change in the pressure chamber (80) which deforms the deformable diaphragm (71) and thereby moves dialysate within said dialysate conduit (20). The controller (31) comprises a computer (135) configured to act on instructions for operation of the pump (90).

Check valves (101,102,103,104) are disposed along the conduit (20) and are configured to, in the outflow mode, allow the dialysate to flow from the peritoneum (60) to the storage chamber (70), and in the inflow mode allow the dialysate to flow from the storage chamber (70) to said sorbent zone (11) for removal of contaminants therein, and further permit the dialysate substantially free of said contaminants to flow back to the peritoneum (60).

The disposable housing is also provided with an enrichment module (12), for dispensing a preselected amount of an enrichment solution into the dialysate, in fluid communication with the conduit (20) via a conduit (13). The enrichment module is also in fluid communication with an enrichment solution reservoir (121). The pump (90) is in fluid communication with a deformable membrane (72) of the enrichment module 12 via conduit connector (40a,40b), when the disposable housing (10) and control housing (30) are in operable engagement. The conduit connector (40a,40b) comprises a first mating part (133f) and a second mating part (133s).

An ammonia sensor (140) is also provided downstream of the sorbent zone (11) to detect any ammonia in the dialysate. Ammonia is detected by the ammonia detector (141) when the disposable housing (10) and control housing (30) are operably coupled to each other.

A degasser in the form of a hydrophobic membrane (150) is also located downstream of the sorbent zone. The external side of the hydrophobic membrane (150) is in fluid communication with a vacuum pump (151) via the conduit connector (40a,40b) when the control housing and disposable housing are operably coupled. As will be appreciated, the degasser may not be necessary when used with a filter device that has a degassing capability (e.g. filter devices 300, 302, 400).

Figure 9:
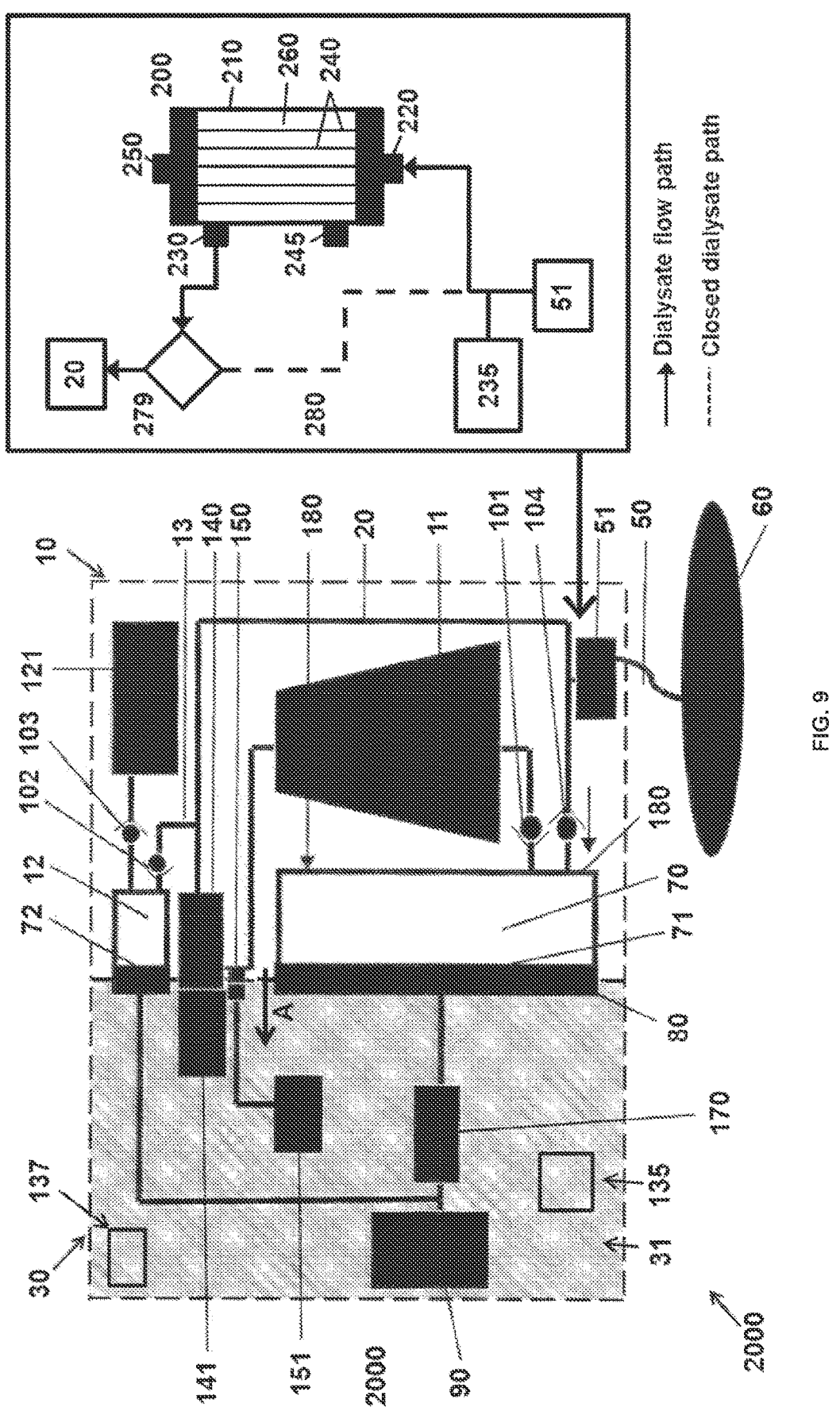
FIG. 9 Depicts the integration of single chamber filter device 200 of the current invention into an example of a peritoneal dialysis device 2000 in outflow mode.
Figure 10:
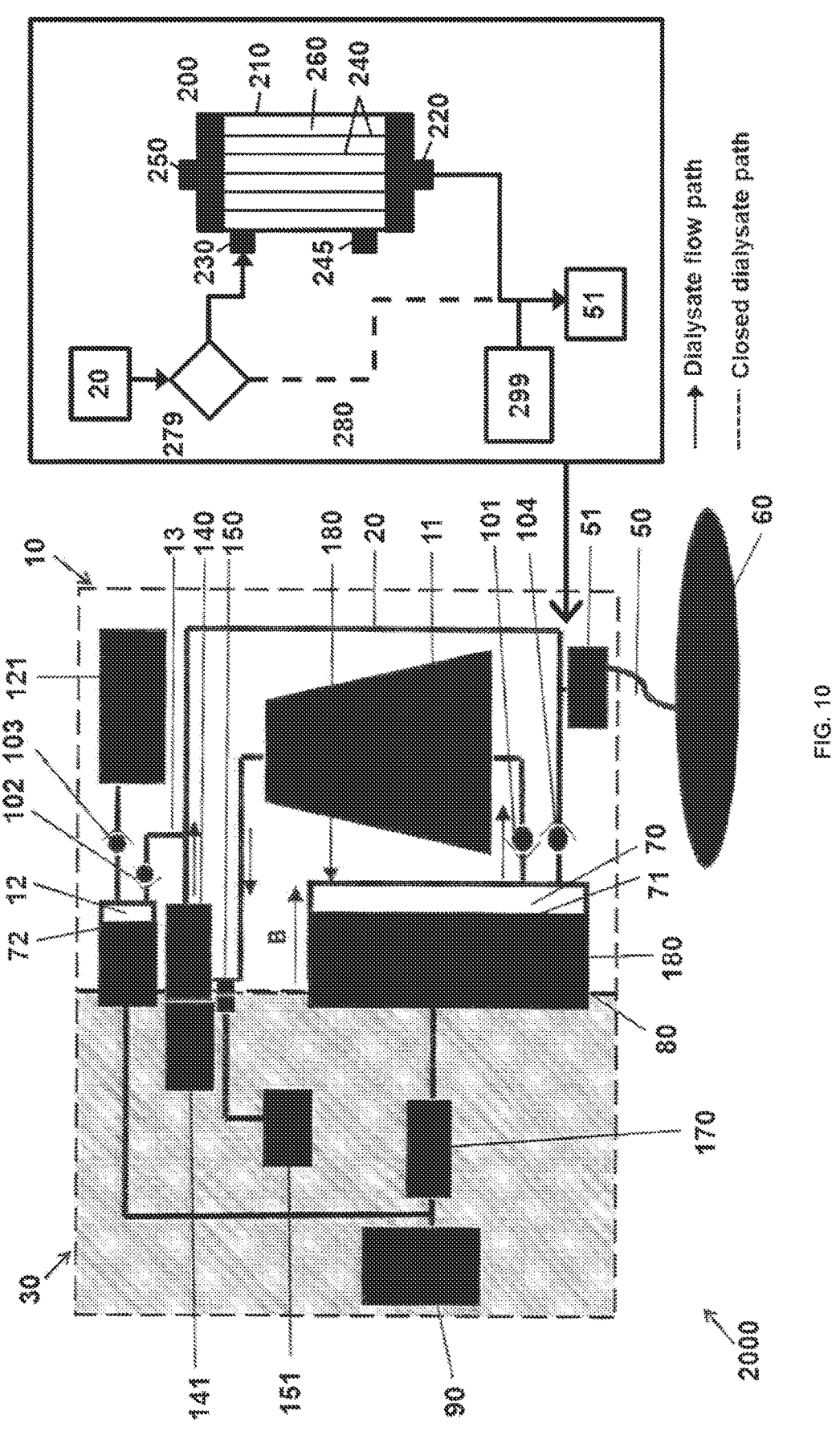
FIG. 10 Depicts the integration of single chamber filter device 200 of the current invention into a peritoneal dialysis device 2000 in inflow washback mode.
Figure 11:
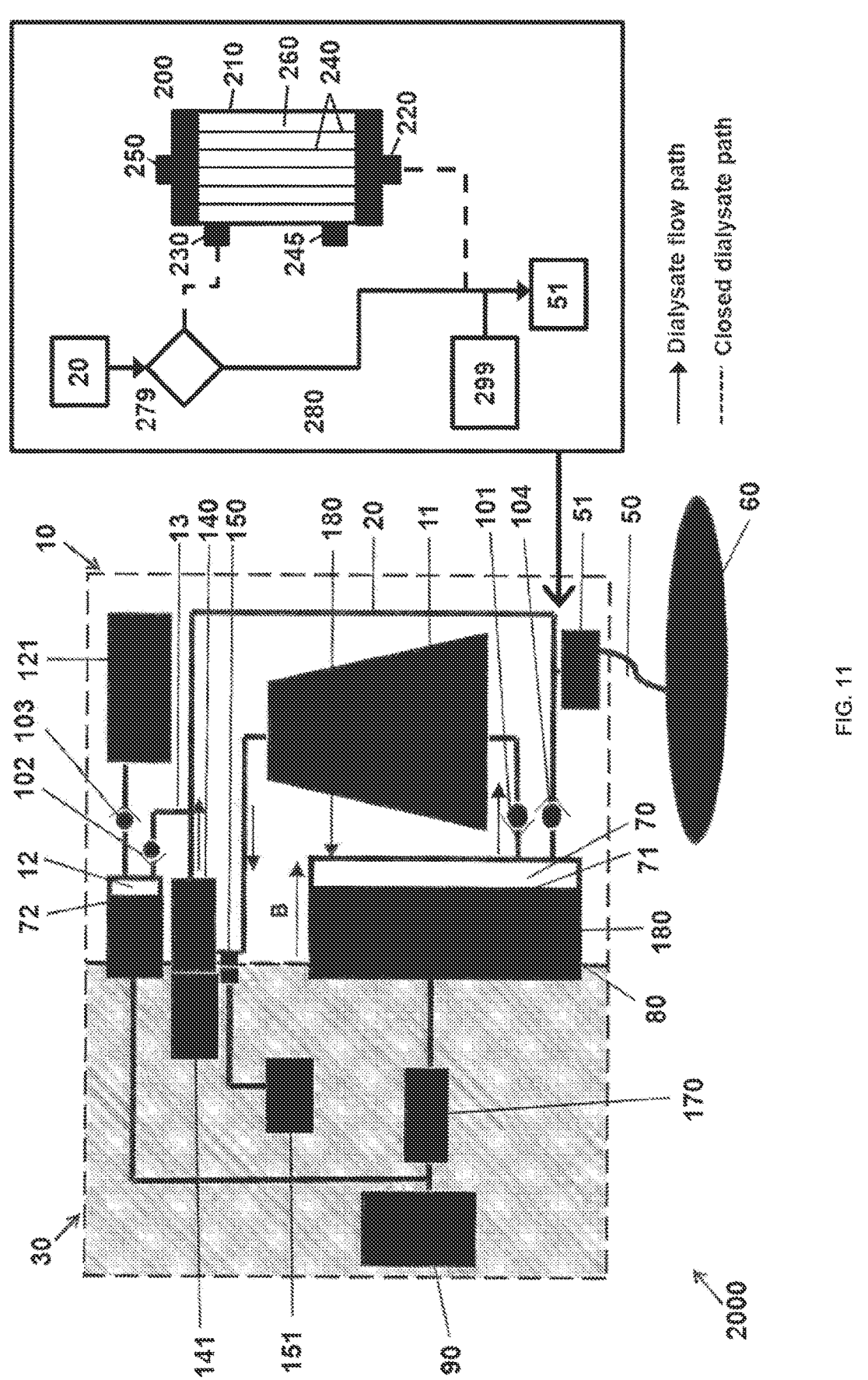
FIG. 11 Depicts the integration of single chamber filter device 200 of the current invention into a peritoneal dialysis device 2000 in inflow bypass mode.

FIGS. 9-11 show how a filter device of the current invention (e.g. the single chamber filter device depicted in FIG. 2) can be integrated into an example of a peritoneal dialysis device.

FIG. 9 depicts an integrated device in outflow mode, showing the disposable housing (10) and control housing (30) operably coupled with each other, operating in an outflow mode, wherein the flow of the dialysate is toward the storage chamber (70) from the peritoneum (60) of a patient. The pump (90) actuates the deformable diaphragm (71), by inducing negative pressure in the pressure chamber (80). The negative pressure in the pressure chamber (80) deforms the deformable diaphragm (71) by biasing the deformable diaphragm (71) in the direction of arrow A and thereby moves dialysate from said peritoneum (60) of the patient into the dialysate conduit (20) via bubble trap (51). The dialysate flows to the storage chamber (70) through check valve (104). A pressure sensor (170) is located in operable communication with the pump (90) to establish a preselected negative pressure within the pressure chamber (80) and to determine if the pressure of the dialysate being withdrawn from the peritoneum (60) is within a safe limit.

The pump (90) operates intermittently under the control of the pressure sensor (170) to maintain the negative pressure in the pressure chamber (80) within a preselected range. Once the storage chamber (70) is full of dialysate, this is detected by the pressure sensor (170), triggering the inversion of the pump direction and thus converting the system to an inflow mode.

The pump 90 is also in fluid communication with a diaphragm (72) integrally formed in a wall of said enrichment module (12). At the same time as the storage chamber (70) is actuated under negative pressure, the enrichment module (12) is also actuated under negative pressure by the pump (90), such that a predetermined amount of an enrichment solution is withdrawn from an enrichment solution reservoir (121) though check valve (103) into the enrichment module (12). Check valve (102) ensures that no dialysate is withdrawn into the enrichment module (12) from the conduit (20).

In order to integrate the single chamber filter (200) into the embodiment of FIGS. 1A-C of US Patent Publication Number 2018/0147338 A1, the filter, switch, bypass line and associated tubing and connectors would be installed between the bubble trap (51) and the conduit (20), as depicted in FIG. 9. In an outflow mode, the spent dialysate would flow from the peritoneum (60), to the bubble trap (51) before entering the filtration circuit. Directed by the switch (279), the spent fluid would initially enter the first port (220) of the filter device (200). The spent dialysate then enters the inner channel of the hydrophilic hollow fibres (240). Due to negative pressure exerted on the exterior surface of the hollow fibres, water and low molecular weight solutes (<40 kDa) are transported from the inner channel of the hollow fibres (240), through the porous wall matrix, to the outer chamber (260) surrounding the exterior of the hollow fibres. Larger solutes such as proteins and fibrin are trapped on the lumen surface of the hollow fibres, preventing their interaction with interior components of the purification system (i.e. sorbent 11). The filtered spent dialysate is then pumped from the second port (230) of the hollow fibre membrane by pump (90) to the storage chamber (70) via conduit (20), through check valve (104). The remaining dialysate treatment process is completed as stated in US 2018/0147338 A1. The duration of outflow mode in this case is governed by the flow rate which the storage chamber is filled (70) and degree of clogging of the filter. An optional additional pressure sensor (235), located before (depicted) or inside bubble trap (51), may be used to monitor the fluidic pressure between the system and the patient, ensuring that the patient line pressure remains within a safe working range. While monitoring pressure sensors (235 and 170), the system can then adjust pump (90) to maintain a sufficient negative pressure in pressure chamber to ensure consistent and efficient regeneration of dialysate.

FIGS. 10 and 11 depicts the integrated device with the single chamber filter device (200) in the first (FIG. 10) and second (FIG. 11) stages of the inflow mode.

The inflow mode for the main dialysis system (2000) is the same in both FIGS. 10 and 11. In the inflow mode of FIG. 10, the flow of the dialysate is from the storage chamber (70) to the peritoneum (60). Once the storage chamber (70) is full, the pump (90) actuates the deformable diaphragm (71), by inducing positive pressure in the pressure chamber (80).

The positive pressure in the pressure chamber (80) deforms the deformable diaphragm (71) by biasing the deformable diaphragm (71) in the direction of arrow B and thereby moves dialysate from the storage chamber (70) and check valve (104) closes preventing dialysate from returning to the peritoneum (60) before being treated to remove contaminants.

The pressure sensor (170) monitors the pressure in the pressure chamber (80) to ensure that the pressure of the dialysate being returned to the peritoneum (60) in the inflow mode is within a safe limit.

The dialysate flows from the storage chamber (70) into the sorbent zone (11) through check valve (101). The regenerated dialysate from the sorbent zone (11) then flows past a degasser in the form of a hydrophobic membrane (150). The external side of the membrane is subjected to negative pressure by a vacuum pump (151) to aid the removal of gas generated during the dialysis procedure. The dialysate then flows through an ammonia sensor (140) which monitors the level of ammonia in the regenerated dialysate, to ensure that the ammonia level does not exceed a safe limit, prior to returning to the peritoneum (60) of a patient. Ammonia is detected by the ammonia detector (141).

The regenerated dialysate then flows past an enrichment module (12). In the inflow mode, the pump (90) actuates the diaphragm (72) of the enrichment module (12), which has previously been primed with a volume of enrichment solution from the enrichment solution reservoir (121), under positive pressure. As the enrichment module (12) is actuated, check valve (103) closes to ensure that the enrichment solution does not flow back into the enrichment solution reservoir (121). The enrichment module (12) then dispenses a preselected amount of enrichment solution containing desired substances, such as electrolytes, osmotic agents, nutrients, medication and the like, into the dialysate conduit (20) through check valve (102) and conduit (13).

The regenerated dialysate then flows back to the peritoneum (60) through the bubble trap (51) and flexible dialysate conduit (50).

As in the outflow mode, the pump (90) is operated intermittently under the control of the pressure sensor (170) to maintain the positive pressure in the pressure chamber (80) within a preselected range. Once the storage chamber is empty of dialysate, the pressure sensor (170) detects this and inverts the pump direction and converts the system to the outflow mode to repeat the dialysis cycle.

In the initial inflow washback phase (as shown in FIG. 10), the regenerated fresh dialysate is transported from conduit (20) by pump (90) to the second filter port (230) via switch 279. Downstream from conduit (20), the fresh dialysate encounters and mixes with spent dialysate from the previous outflow. The mixture of fresh and spent dialysate (the combination of which make up the washback fluid) enters the filter chamber (260), exerting a positive fluidic pressure on the exterior surface of the hollow fibres (240). Due to this positive fluidic pressure, low molecular weight solutes such as water, glucose and electrolytes are forced through the porous wall matrix through to the inner channel of the hydrophilic fibres (240). During this process, any proteins or biological material trapped on the lumen of the fibres are dislodged, de-fouling the inner pores of the fibre and restoring the original filter surface area. The washback fluid exits the filter through port (220) and passes through the bubble trap (51) re-enters the peritoneum (60). The volume of washback fluid (and hence duration of washback time) is optimised such that a minimum of spent fluid is returned to the patient, while ensuring patency of the filter is maintained for the next outflow cycle. An optional additional pressure sensor (299), located before (depicted) or inside bubble trap (51), may be used to monitor the fluidic pressure between the system and the patient, ensuring that the patient line pressure remains within a safe working range.

After the inflow washback phase is over, the inflow bypass phase commences and this is depicted in FIG. 11. The regenerated fresh dialysate is transported from conduit (20) by pump (90) to the bypass line 280 via switch 279. Downstream from conduit (20), the fresh dialysate encounters and mixes with a small amount of washback fluid from the previous inflow washback cycle. Due to routing by switch 279, the predominantly fresh dialysate bypasses the chamber 260 and instead passes through the bubble trap (51) and directly re-enters the peritoneum 9 via bypass line 280. The volume of inflow bypass fluid is optimised such that a maximum of fresh fluid is returned to the patient, in order to sustain a sufficient dialysate/serum gradient for efficient toxin removal and electrolyte control. An optional additional pressure sensor 299, located before (depicted) or inside bubble trap (51), may be used to monitor the fluidic pressure between the system and the patient, ensuring that the patient line pressure remains within a safe working range.

Figure 18:
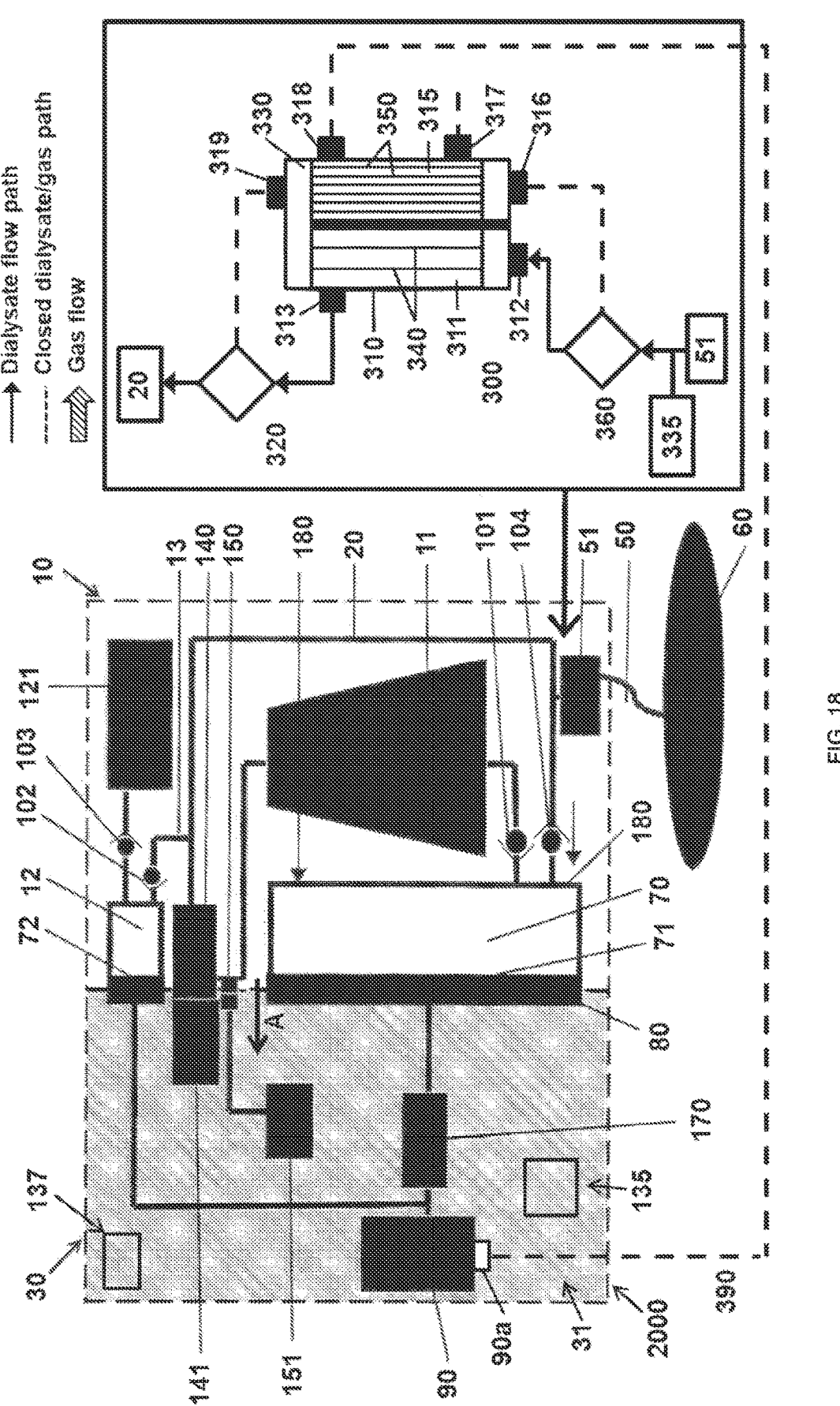
FIG. 18 Depicts the integration of double chamber filter device 300 of the current invention into an example of a peritoneal dialysis device 2000 in outflow mode.
Figure 19:
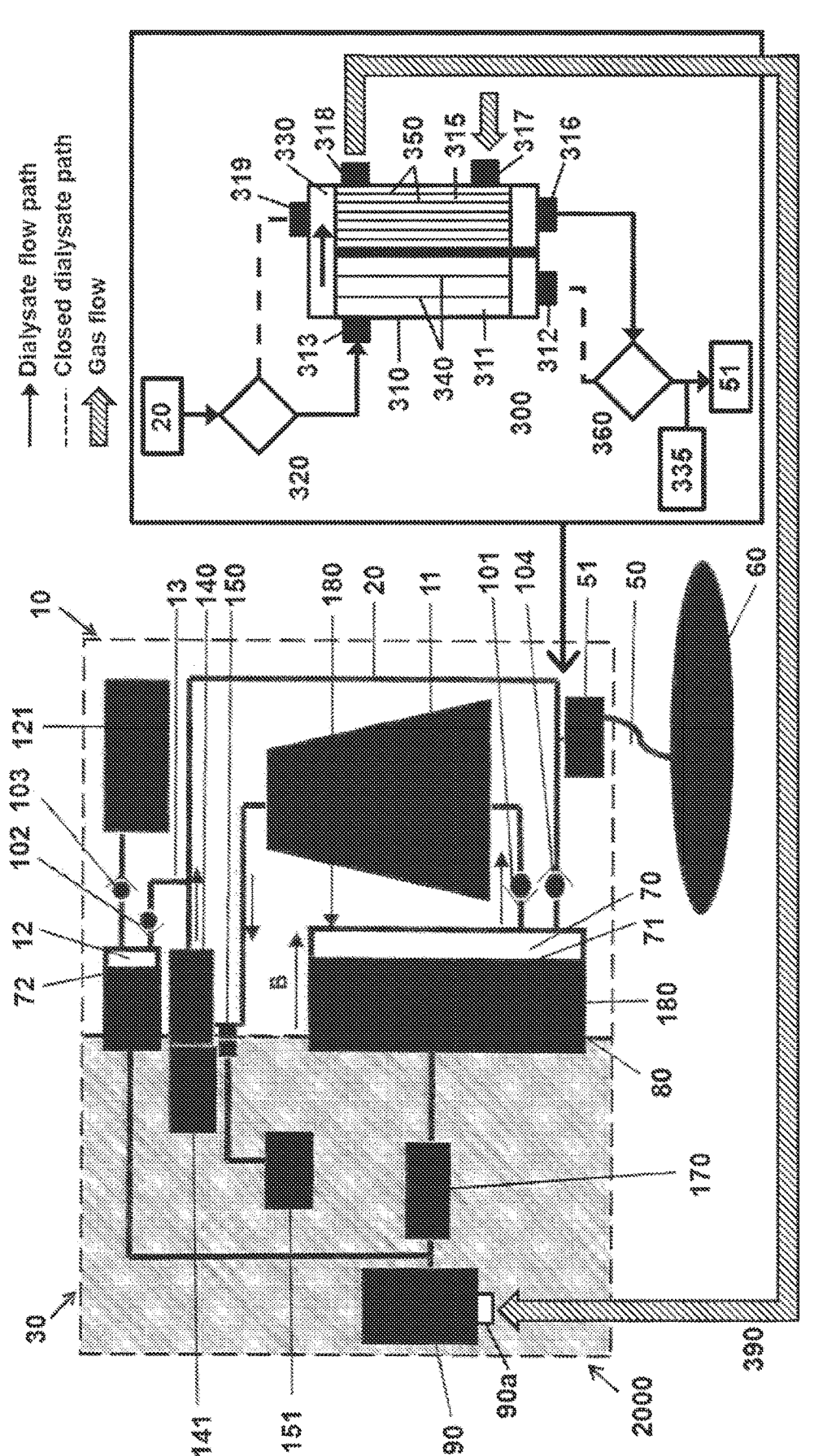
FIG. 19 Depicts the integration of double chamber filter device 300 of the current invention into a peritoneal dialysis device 2000 in inflow washback mode.
Figure 20:
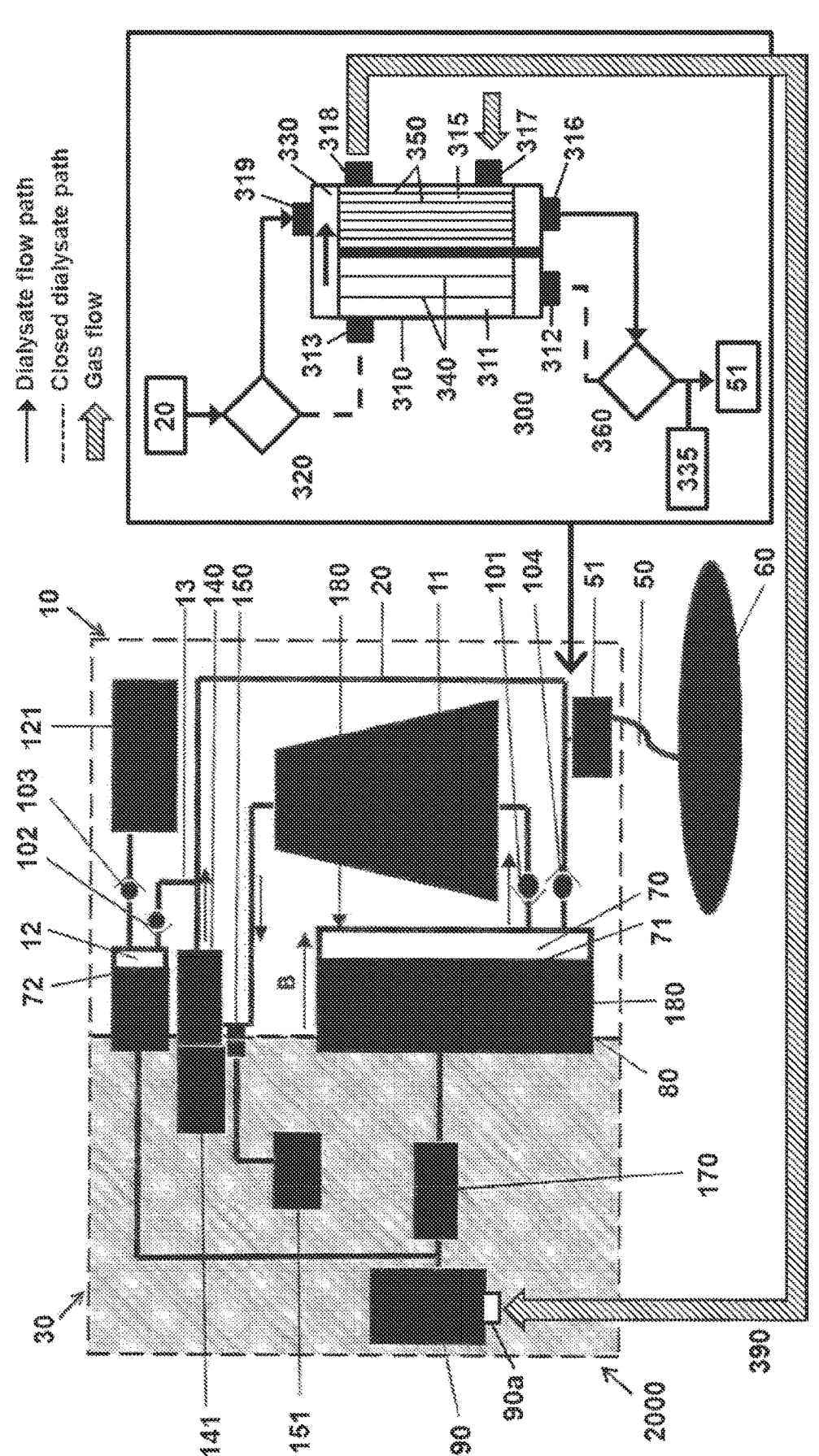
FIG. 20 Depicts the integration of double chamber filter device 300 of the current invention into a peritoneal dialysis device 2000 in inflow bypass mode.

FIG. 18-20 shows how another embodiment of the filter device of the current invention (e.g. the double-chambered filter device depicted in FIG. 4) can be integrated into an example of a peritoneal dialysis device to provide a peritoneal dialysis system according to the invention.

FIG. 18 depicts an integrated device in outflow mode. The main dialysis device (2000) is essentially identical to that described for FIG. 9 and so this will not be described again for brevity. In order to integrate the double chamber filter into the embodiment of FIGS. 1A-C of US Patent Publication Number 2018/0147338 A1, the filter, switch, bypass line and associated tubing and connectors would be installed between the bubble trap (51) and the conduit (20), as depicted in FIG. 18. Additionally, an air conduit (390) is installed to connect the pump air inlet (90*a*) to outlet port (318) of the filter, thus enabling the pump to draw air in from inlet port (317). This provides a sweep gas flowing through chamber (315) under negative pressure during inflow. During outflow, the pump may vent air through (317) or another outlet depending on the pump design. In an alternative embodiment, an external source of a suitably biocompatible sweep gas can be provided (such as a mixture of $O_2/N_2$ or purified compressed air), or a source of negative pressure at 318, or a combination of both.

In an outflow mode (FIG. 18), the spent dialysate would flow from the peritoneum (60), to the bubble trap (51) before entering the filtration circuit. Directed by the switch (360), the spent fluid would initially enter the first port 312 of the filter device 300. The spent dialysate then enters the inner channel of the hydrophilic hollow fibres 340. Due to negative pressure exerted on the exterior surface of the hollow fibres, water and low molecular weight solutes (e.g. <40 kDa) are transported from the inner channel of the hollow fibres 340, through the porous wall matrix, to the outer chamber 311 surrounding the exterior of the hollow fibres. Again, it is noted that a positive pressure could be used instead to achieve the same effect. Larger solutes such as proteins and fibrin are trapped on the lumen surface of the hollow fibres, preventing their interaction with interior components of the purification system 270. The filtered spent dialysate is then pumped from the second port 313 of the hollow fibre membrane by pump (90) to the storage chamber (70) via and conduit (20), through check valve (104). The remaining dialysate treatment process is completed as stated in US 2018/0147338 A1. The duration of outflow mode in this case is governed by the flow rate which the storage chamber is filled (70) and degree of clogging of the filter. An optional additional pressure sensor (335), located before (depicted) or inside bubble trap (51), may be used to monitor the fluidic pressure between the system and the patient, ensuring that the patient line pressure remains within a safe working range. While monitoring pressure sensors (335 and 170), the system can then adjust pump (90) to maintain a sufficient negative pressure in pressure chamber to ensure consistent and efficient regeneration of dialysate.

FIGS. 19 and 20 depict the integrated device having the double chamber filter device 300 in the first (FIG. 19) and second (FIG. 20) stages of the inflow mode, also known as the inflow washback and inflow bypass mode, respectively.

The inflow mode for the main dialysis system (2000) in both FIGS. 19 and 20 are essentially identical to that described for FIGS. 10 and 11, and so this will not be described again for brevity.

In the initial inflow washback phase (as shown in FIG. 19), the regenerated fresh dialysate is transported from conduit (20) by pump (90) to the second filter port (313) via switch (320). Downstream from conduit (20), the fresh dialysate encounters and mixes with spent dialysate from the previous outflow. The mixture of fresh and spent dialysate (the combination of which make up the washback fluid) enters the filter chamber (311), exerting a positive fluidic pressure on the exterior surface of the hollow fibres (340). Due to this positive fluidic pressure, water and low molecular weight solutes such as glucose and electrolytes are forced through the porous wall matrix through to the inner channel of the hydrophilic fibres (340). During this process, any proteins or biological material trapped on the lumen of the fibres are dislodged, de-fouling the inner pores of the fibre and restoring the original filter surface area. The washback fluid is routed through the headspace (330) and into the inner channel of the hydrophobic fibres (350) housed in the second chamber (315). As mentioned above, the washback fluid may be degassed through use of a sweep gas though the inlet port (317), or negative pressure can be applied through the outlet port (318), or a combination of both. In FIG. 19, pump (90) provides a constant flow of air under negative pressure at the outlet port (318), which degasses the fluid passing through the hydrophobic hollow fibres (350) in chamber 315. The degassed washback fluid is purged from the filter through port 316, passes through the bubble trap (51) and re-enters the peritoneum (60) via switch 360. The volume of washback fluid is optimised such that a minimum of spent fluid is returned to the patient, while ensuring patency of the filter is maintained for the next outflow cycle. An optional additional pressure sensor (335), located before (depicted) or inside bubble trap (51), may be used to monitor the fluidic pressure between the system and the patient, ensuring that the patient line pressure remains within a safe working range.

After the inflow washback phase is over, the inflow bypass phase commences and this is depicted in FIG. 20. The regenerated fresh dialysate is transported from conduit (20) by pump (90) to port 319 via switch 320. Due to routing by switch 320, the fluid bypasses the first chamber (311), and instead enters the inner channel of the hydrophobic fibres (350), which are enclosed in the second chamber (315). Downstream from purification system (e.g. sorbent 11), the fresh dialysate encounters and mixes with a small amount of washback fluid from the previous inflow washback cycle. The predominantly fresh dialysate enters the inner channel of the hydrophobic fibres (350) and is degassed as outlined above. The degassed fresh dialysate is then pumped through filter outlet port 316, through the bubble trap (51) and re-enters the peritoneum (60) via switch 360. The volume of inflow bypass fluid is optimised such that a maximum of fresh fluid is returned to the patient, in order to sustain a sufficient dialysate/serum gradient for efficient toxin removal and electrolyte control. An optional additional pressure sensor 335, located before (depicted) or inside bubble trap (51), may be used to monitor the fluidic pressure between the system and the patient, ensuring that the patient line pressure remains within a safe working range.

As will be appreciated, the bubble trap discussed above may not always be necessary. While most automated peritoneal dialysis systems include a bubble trap or a bubble sensor to prevent air from going to the patient, not all forms of peritoneal dialysis incorporate such a feature. For example, Continuous Ambulatory Peritoneal Dialysis (CAPD), which involves the patient filling themselves from a bag by gravity, does not include a bubble trap or sensing mechanism. Given this, the bubble trap may or may not be present in the peritoneal dialysis systems that form embodiments of the invention.

It will be appreciated that the system described above can be adapted to work with the other filter devices disclosed herein. In addition, it will be understood that other peritoneal dialysis systems can be adapted (or designed) to function with the filter devices disclosed herein.

Figure 12:
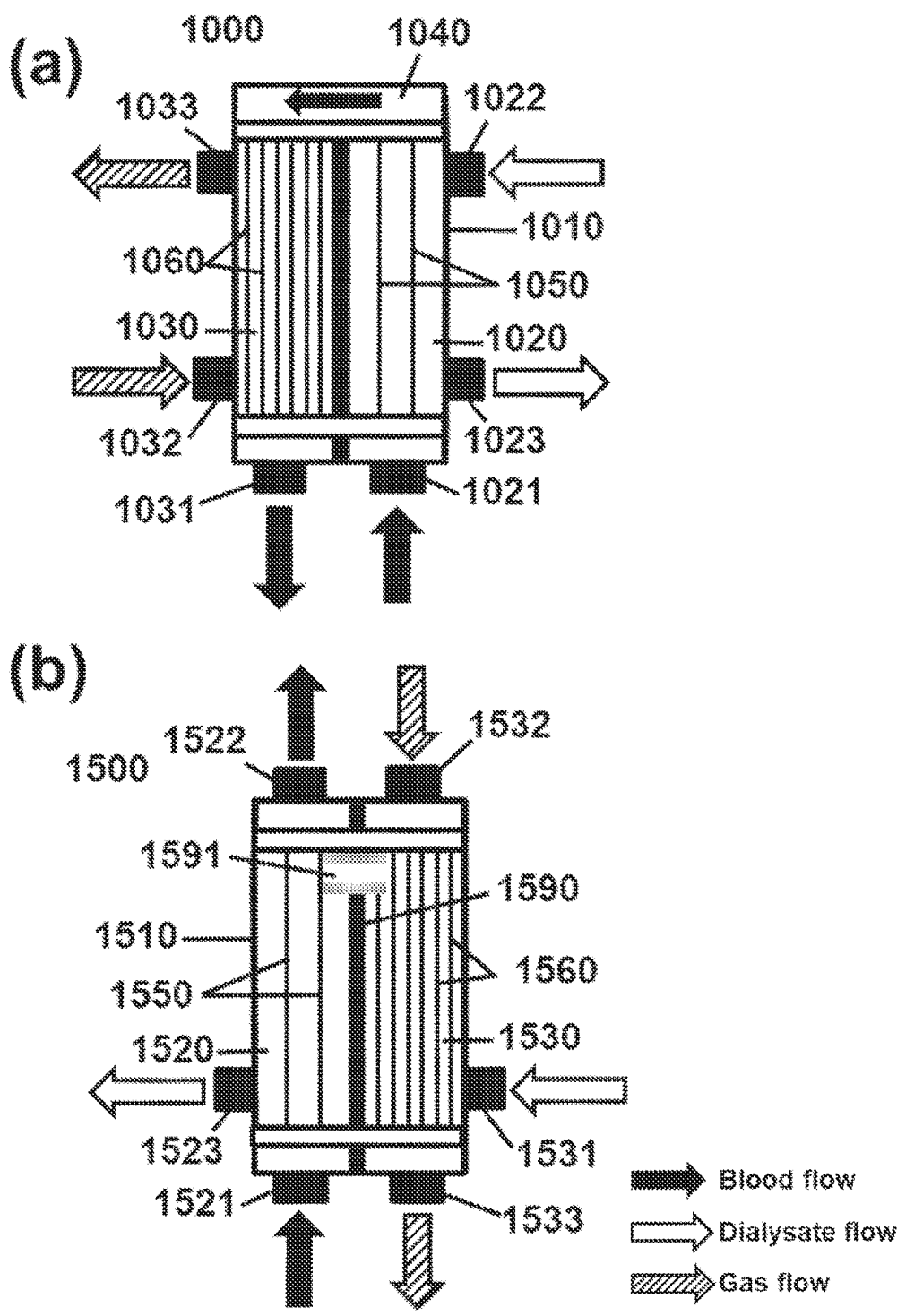
FIG. 12 Depicts: (a and b) configurations of haemodialysis device 1000 and 1500, respectively, of the current invention.

It will also be appreciated that the peritoneal dialysis filter device and post-filtration system may be provided as a kit of parts containing both components. This is described in the summary of invention section above in more detail, but is omitted here for the sake of brevity. The currently-disclosed filter devices can also be used in a haemodialysis system. In this regard, there is also disclosed a haemodialysis device 1000 (as shown in FIG. 12a), which comprises:

a housing 1010 comprising:

an exchange compartment 1020 having a blood inlet port 1021, a dialysate inlet port 1022 and a dialysate outlet port 1023;

a blood degassing compartment 1030 having a blood outlet port 1031, a degassing gas inlet port 1032 and a negative pressure/gas outlet port 1033;

a head-space cavity portion 1040 that fluidly connects the exchange compartment 1020 to the blood degassing compartment 1030;

a first hollow fibre membrane 1050 formed from hollow hydrophilic fibres within the exchange compartment 1020 of the housing 1010, where each of the fibres have an inner surface and an outer surface and where the inner surface of the hollow hydrophilic fibres are aligned co-axially with respect to the alignment of the blood inlet port 1021 and the outer surface of the hollow fibres is aligned perpendicularly with respect to the alignment of the dialysate inlet 1022 and outlet 1023 ports;

a second hollow fibre membrane 1060 formed from hollow hydrophobic fibres within the blood degassing compartment 1030 of the housing 1010, where each of the fibres have an inner surface and an outer surface, where the inner surface of the hollow hydrophobic fibres are aligned co-axially with respect to the alignment of the blood outlet port 1031 and the outer surface of the hollow fibres is aligned perpendicularly with respect to the alignment of the gas inlet 1032 and/or negative pressure 1033 ports. This device may also include a device for regenerating dialysate.

Figure 13:
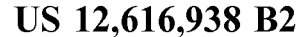
FIG. 13 Depicts an embodiment of haemodialysis device 1000 for integrated sorbent-based continuous renal replacement therapy (CRRT) in: (a) full view; and (b) top view.

This embodiment will now be described by reference to FIGS. 13a and b. The device depicted in FIG. 13a further includes a sorbent compartment 1070. In FIG. 13a, dialysate fluid will be continuously drawn from a dialysate reservoir 1071, and enter port 1072, the dialysate will then pass through the sorbent in sorbent compartment 1070. As it does this, it becomes fresh dialysate, which exits from port 1074. On the way to the exchange compartment 1020, the dialysate line is met by an infusate line whereby the concentration of essential cations $Ca^{2+}$, $Mg^{2+}$, $K^+$ will be restored to a predetermined level by the addition of concentrate contained in an infusate module (infusate module and pump not shown). As will be appreciated, the infusate can be simply supplied by a concentrate bag (e.g. controlled manually). The regenerated dialysate will then enter exchange compartment 1020 through port 1022 and so will pass over the outer surface of the hollow hydrophilic fibres 1050, while blood enters through port 1021 and runs through the lumen of said fibres in a parallel direction (this is because the fibres are arranged co-axially relative to port 1021). As such, the dialysis process occurs by a mass exchange mechanism between blood and the dialysate fluid. The cleaned blood will pass over the headspace 1040 and enters the blood degassing compartment 1030, which houses hydrophobic hollow fibres 1060. Again, the blood runs through the lumen of the fibres. In the blood degassing compartment 1030, blood can be degassed before it is returned to the subject (via an outlet port 1024), through the application of a sweep gas inlet 1032 and a gas outlet 1033 and/or by the application of negative pressure (through outlet 1033). As will be appreciated, the gas and/or negative pressure interact directly with the outer surface of the hollow fibres 1060. As will also be appreciated, when a sweep gas, is used that contains oxygen, the blood can be infused with $O_2$ to replace $CO_2$. Spent dialysate will return to the reservoir 1071 through dialysate outlet port 1023. Pumps are used to control the flow of blood to/from the patient (pump 1091), draw dialysate toward the infusate module (pump 1092) and returning spent dialysate to the dialysate reservoir (pump 1093). A top view of the filter device is as shown in FIG. 13b.

Figure 14:
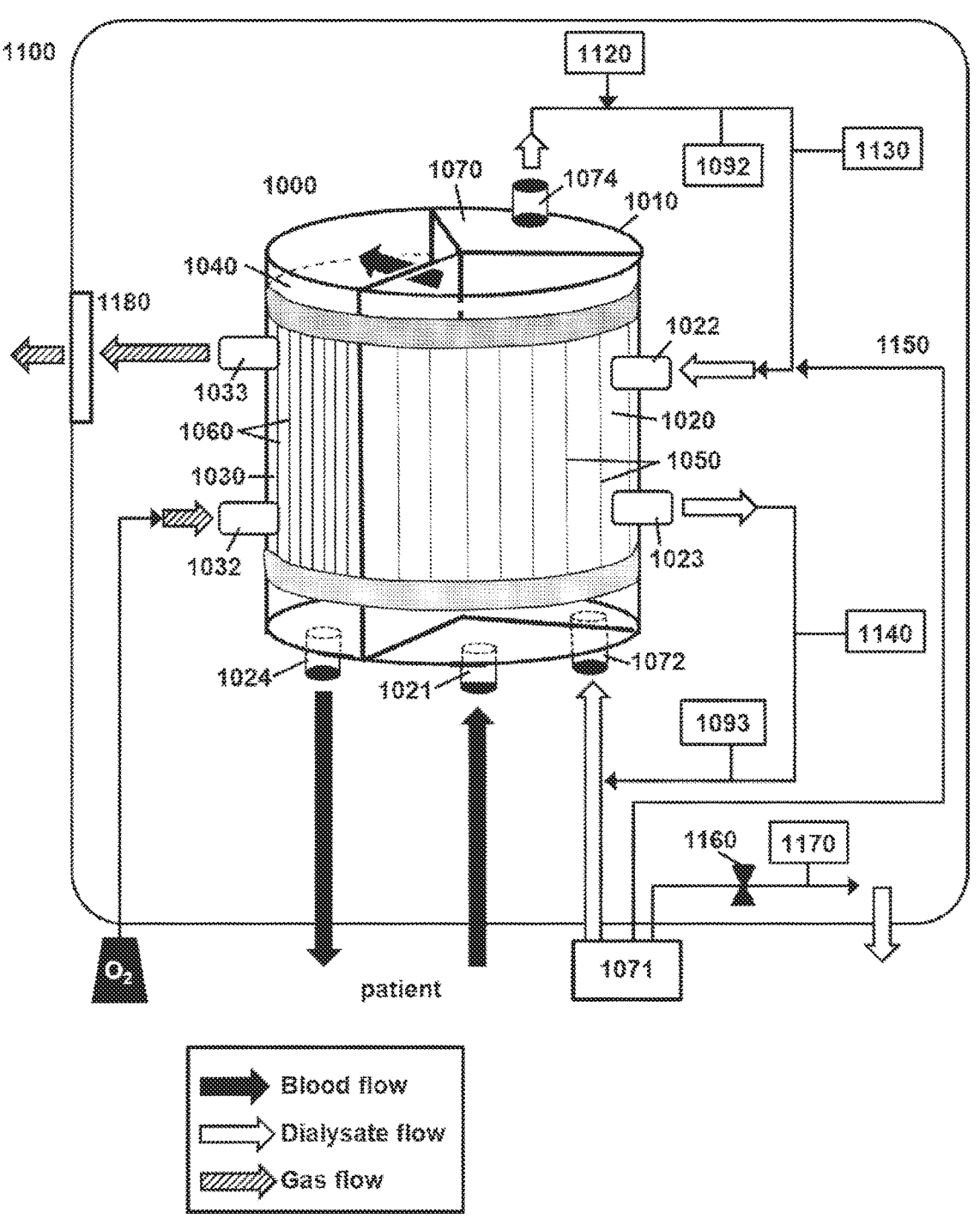
FIG. 14 Depicts the integration of the haemodialysis device 1000 into a haemodialysis system with other components.

The device 1000 depicted in FIG. 13a can be further integrated into an example of a haemodialysis system with other components, as shown in FIG. 14. There is no difference in the operation of the filter device, which can be understood by the above description for FIG. 13a and so is not discussed in detail here.

FIG. 14 shows a haemodialysis device housing 1100 comprising the filter device 1000 with other components. The dialysate may be drawn from an external dialysate reservoir 1071 into the sorbent component 1070 via port 1072, primarily controlled by pump 1092. The fresh dialysate, which exits from port 1074, is restored of essential cations by an infusate module, controlled by an infusate pump 1120. Other control modules 1130 (such as a heater, pump 1092) and returning spent dialysate flow meter, conductivity meter, temperature meter and ultrafiltration control) can be integrated in the dialysate flow path between the outlet port 1074 and inlet port 1022 to monitor the properties of the regenerated dialysate prior to feeding it into the exchange compartment 1020. This can provide information on the efficiency and capacity of the sorbent in removing metabolic waste products from the dialysate, and when to replace the sorbent component or filter device.

After the exchange compartment 1020, the spent dialysate is pumped out and rechannelled back into the sorbent component 1070 via port 1072. Similarly, control modules 1140 (i.e. blood leak detector and ultrafiltration meter) may be installed in the flow path between outlet port 1023 and inlet port 1072 to monitor the properties of the spent dialysate. This provides information on the integrity of the hollow hydrophilic fibres 1050, and whether cross-mixing of the dialysate and blood has occurred. In an event that the sorbent component 1070 is exhausted, the dialysate can be channelled from the dialysate reservoir 1071 through a bypass line 1150 to the inlet port 1022 of the exchange component 1020. Further, dialysate can be released from the dialysate reservoir 1071 (out of the housing 1100), and this is controlled by a reservoir drain valve 1160, and a pump 1170.

In the blood degassing component 1060, blood can be degassed before it is returned to the subject (via an outlet port 1024), through the application of a sweep gas inlet 1032 (from an external gas source) and a gas outlet 1033, and/or by the application of negative pressure (through outlet 1033). The gas can be released through a gas outlet 1180 in the housing, or by the application of negative pressure at 1180.

In an alternative arrangement, there is also disclosed herein a further haemodialysis device 1500 (as shown in FIG. 12b), which comprises:

a housing 1510 comprising:

an exchange compartment 1520 having a blood inlet port 1521, a blood outlet port 1522 and a dialysate outlet port 1523;

a dialysate degassing compartment 1530 having a dialysate inlet port 1531, a degassing gas inlet port 1532 and a negative pressure/gas outlet port 1533;

a wall 1590 defining a fluid-impermeable boundary between the exchange compartment 1520 and the dialysate degassing compartment 1530;

a dialysate fluid portal 1591 allowing a dialysate to move from the dialysate degassing compartment 1530 to the exchange compartment 1520;

a first hollow fibre membrane 1550 formed from hollow hydrophilic fibres within the exchange compartment of the housing, where each of the fibres have an inner surface and an outer surface and where the inner surface of the hollow hydrophilic fibres are aligned co-axially with respect to the alignment of the blood inlet and outlet ports, and the outer surface of the hollow fibres is aligned perpendicularly with respect to the alignment of the dialysate outlet port 1523; and a second hollow fibre membrane 1560 formed from hollow hydrophobic fibres within the dialysate degassing compartment of the housing, where each of the fibres have an inner surface and an outer surface, where the inner surface of the hollow hydrophobic fibres are aligned co-axially with respect to the alignment of the degassing gas inlet port 1532 and the negative pressure/gas outlet port 1533, and the outer surface of the hollow fibres is aligned perpendicularly with respect to the alignment of the dialysate inlet port 1531 and the dialysate fluid portal 1591. This device may also include a device for regenerating dialysate.

It will be appreciated that this embodiment operates by analogy to those described hereinbefore. That is, dialysate enters through inlet port 1531 into the degassing chamber, where it is degassed by the use of a sweep gas (e.g. air, oxygen or a mixture of air and other gasses, such as nitrogen), such that unwanted gasses (e.g. $CO_2$) are replaced at least in part by oxygen. The dialysate encounters only the outer surface of the hydrophobic hollow fibres 1560, while the degassing gas passes through the lumen of said fibres. The degassing chamber 1530 is separated from the exchange chamber by a fluid-impenetrable wall 1590, which contains a fluid portal 1591 in an upper region thereof. As will be appreciated, instead of a portal though part of the wall, the wall could instead be formed as a weir. In order to enter the exchange chamber 1520, the dialysate flows through fluid portal 1591 and hence into the exchange chamber, where it will pass over the outer surface of the hollow hydrophilic fibres 1550, while blood enters through port 1521 and runs through the lumen of said fibres in a parallel direction (this is because the fibres are arranged co-axially relative to port 1051). As such, the dialysis process occurs by a mass exchange mechanism between blood and the dialysate fluid. The cleaned blood may then exit through blood outlet port 1522. As will be appreciated, the general function of the filter device depicted in FIG. 12b is the same as that depicted in FIG. 12a and features not described above may be considered to be incorporated, where appropriate, by analogy.

Figure 15:
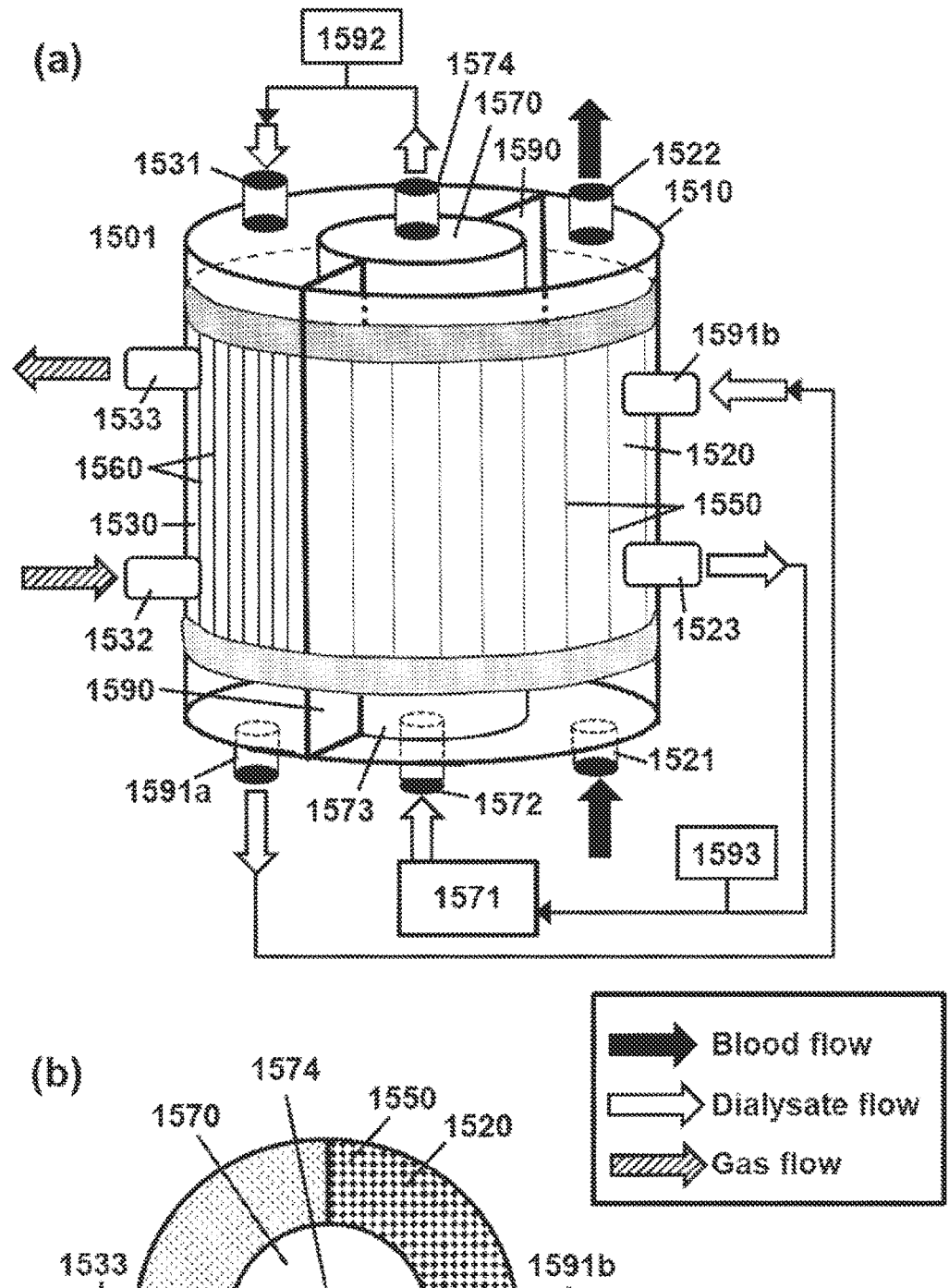
FIG. 15 Depicts an embodiment of haemodialysis device 1501 for integrated sorbent-based hemodialysis with degassing of dialysate in: (a) full view; and (b) top view.

There is also disclosed a further haemodialysis device 1501 (as shown in FIGS. 15a and b), which comprises:

a housing 1510 comprising:

an exchange compartment 1520 having a blood inlet port 1521, a blood outlet port 1522, a first dialysate inlet port 1591b and a first dialysate outlet port 1523;

a dialysate degassing compartment 1530 having a second dialysate inlet port 1531, a second dialysate outlet port 1591a, a degassing gas inlet port 1532 and a negative pressure/gas outlet port 1533;

a wall 1590 defining a fluid-impermeable boundary between the exchange compartment 1520 and the dialysate degassing compartment 1530;

a first hollow fibre membrane 1550 formed from hollow hydrophilic fibres within the exchange compartment of the housing, where each of the fibres have an inner surface and an outer surface and where the inner surface of the hollow hydrophilic fibres are aligned co-axially with respect to the alignment of the blood inlet 1521 and outlet 1522 ports, and the outer surface of the hollow fibres is aligned perpendicularly with respect to the alignment of the first dialysate inlet 1591b and outlet 1523 ports; and a second hollow fibre membrane 1560 formed from hollow hydrophobic fibres within the dialysate degassing compartment 1530 of the housing, where each of the fibres have an inner surface and an outer surface, where the inner surface of the hollow fibres is aligned co-axially with respect to the alignment of the second dialysate 1531 inlet and outlet 1591a ports and the outer surface of the hollow fibres is aligned perpendicularly with respect to the alignment of the degassing gas inlet port 1532 and the negative pressure/gas outlet port 1533, optionally wherein the device further comprises a device for regenerating dialysate 1570.

This embodiment will now be described by reference to FIGS. 15a and b. The device depicted in FIG. 15a further includes a sorbent compartment 1570. Dialysate fluid will be continuously drawn from the dialysate reservoir 1571, and enter port 1572, which then passes through the sorbent in sorbent compartment 1573 and becomes fresh dialysate that exits through port 1574. On the way to the degassing compartment 1530, the dialysate line is met by an infusate line whereby the concentration of essential cations $Ca^{2+}$, $Mg^{2+}$, $K^+$ will be restored to a predetermined level by the addition of concentrate contained in an infusate module (infusate module and pump not shown). As will be appreciated, the infusate can be simply supplied by a concentrate bag (e.g. controlled manually). The replenished fluid will then enter degassing compartment 1530 (via port 1531), which houses hydrophobic hollow fibres 1560, where it is degassed through the application of a sweep gas inlet 1532 and a gas outlet 1533 and/or by the application of negative pressure (through outlet 1533). As will also be appreciated, when a sweep gas that contains oxygen is used, the blood can be infused with $O_2$ to replace $CO_2$. The fresh dialysate then exits through dialysate fluid portal 1591a and enters through dialysate fluid portal 1591b into the exchange compartment 1520, where blood is passing through the lumen of hollow hydrophilic fibres 1550, following entry through blood inlet port 1521. As before, the dialysis process occurs by a mass exchange mechanism between blood and the dialysate fluid. Blood then exits through blood outlet port 1522 and the spent dialysate fluid returns to the dialysate reservoir through dialysate outlet port 1523. Pumps are used to control the flow of blood to/from the patient (not shown), transporting dialysate towards the infusate module (if such a module is present; pump 1592) and returning spent dialysate to the dialysate reservoir (pump 1593). A top view of the filter device 1501 is as shown in FIG. 15b.

Figure 16:
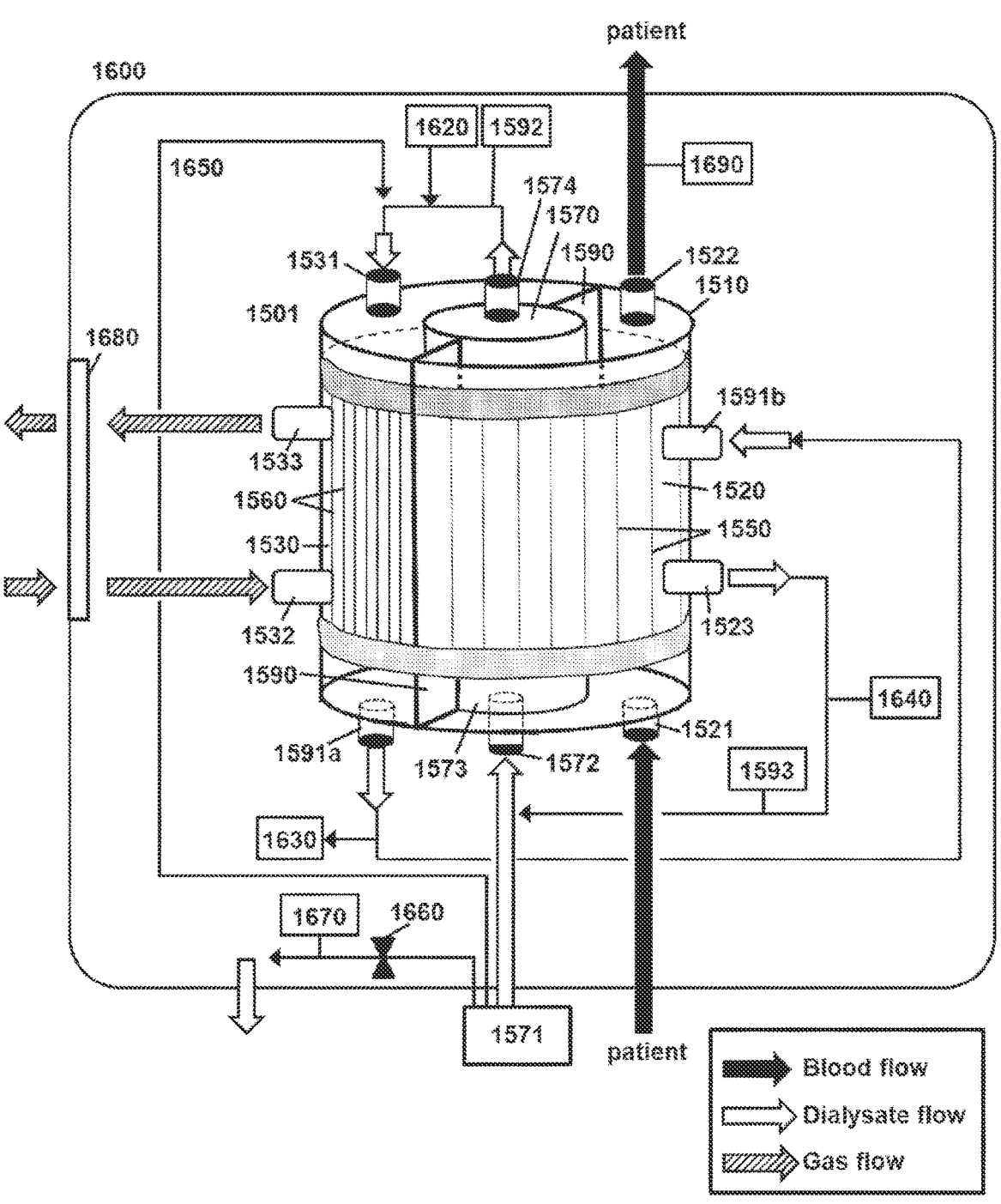
FIG. 16 Depicts integration of the haemodialysis device 1501 into a haemodialysis system with other components.

The filter device 1501 depicted in FIG. 15a can be further integrated into an example of a haemodialysis system with other components, as shown in FIG. 16. There is no difference in the operation of the filter device, which can be understood by the above description for FIG. 15a and so is not discussed in detail here.

FIG. 16 shows a haemodialysis device housing 1600 comprising the filter device 1501 with other components. The dialysate may be drawn from an external dialysate reservoir 1571 into the sorbent component 1570 via port 1572, primarily controlled by pump 1592. The fresh dialysate, which exits from port 1574, is then topped up with the necessary nutrients by an infusate module, controlled by an infusate pump 1620. The replenished fluid will then enter degassing compartment 1530 (via port 1531), which houses hydrophobic hollow fibres 1560, where it is degassed through the application of a sweep gas inlet 1532 and a gas outlet 1533 and/or by the application of negative pressure (through outlet 1533). The gas can be supplied or released through a gas outlet 1680 in the housing. The fresh dialysate then exits through the dialysate outlet 1591a and enters through dialysate inlet 1591b into the exchange compartment 1520. Other control modules 1630 (such as a heater, flow meter, conductivity meter, temperature meter and ultrafiltration control) may be integrated in the dialysate flow path between the dialysate outlet 1591a and inlet 1591b, so as to monitor the properties of the regenerated dialysate prior to entering into the exchange compartment 1520. This provides information on the efficiency and capacity of the sorbent in removing metabolic waste products from the dialysate, and when to replace the sorbent component or filter device.

After the exchange compartment 1520, the spent dialysate is pumped out (i.e. controlled by pump 1593) and rechannelled back into the sorbent component 1570 via port 1572. Similarly, control modules 1640 (i.e. blood leak detector and ultrafiltration meter) may be installed in the flow path between outlet port 1523 and inlet port 1572 to monitor the properties of the spent dialysate. This provides information on the integrity of the hollow hydrophilic fibres 1550, and whether cross-mixing of the dialysate and blood has occurred. In an event that the sorbent component 1570 is exhausted, the dialysate can be channelled from the dialysate reservoir 1571 through a bypass line 1650 to the inlet port 1531 of the degassing compartment 1530. Further, where necessary, the dialysate may be released from the dialysate reservoir 1571 (out of the housing 1600), and this is controlled by a reservoir drain valve 1660, and a pump 1670.

In the degassing compartment 1530, the dialysate can be degassed before it is channelled to the exchange compartment 1520 (via an outlet port 1591*a* and inlet port 1591*b*), through the application of a sweep gas inlet 1532 (from an external gas source) and a gas outlet 1533, and/or by the application of negative pressure (through outlet 1680). As will be appreciated, when a sweep gas that contains oxygen is used, the blood can be infused with $O_2$ to replace $CO_2$. The oxygenated dialysate is then channelled into the exchange compartment 1520 to allow oxygen to be transferred to the blood flowing through the hydrophilic fibres 1550. The cleaned and oxygenated blood may then exit through blood outlet port 1522 and return to the subject.

The filters described herein have a number of advantages that enable them to enhance existing dialysis therapies, including improvements in clinical efficacy and device efficiency in peritoneal dialysis, haemodialysis, ICU continuous renal replacement therapy (CRRT) dialysis. These advantages include, but may not be limited to, the following.

(1) Improve therapeutic safety and functionality—$CO_2$/$O_2$ control. The filter disclosed herein may also provide a degassing and/or oxygenation function to the dialysis machine it is affixed to. By making these features an integral function of the filter disclosed herein, the safety risk to subjects using the machine is reduced, while offering additional treatment options and minimising the overall device footprint (i.e. by negating the need for a separate degassing or oxygenation machine, thereby reducing the overall footprint of the systems needed to provide therapy). A reduced device footprint is one of the most critical elements for the development of a wearable dialysis machine, as well as for use in intensive care unit (ICU) settings, which often have a tight budget for space.

(2) Improve therapeutic efficacy—PBUT removal. The filter solution, disclosed herein makes use of a non-drug dependent method to remove PBUTs. This may be achieved by adding an activated carbon filter in the inflow path before dialysate flows back to the peritoneum, as discussed in more detail herein.

(3) Improve therapeutic efficiency—the filter disclosed herein may be operated using new washback schemes that counteract and prevent clogging of the flow path (e.g. by bound proteins and/or excreted leukocytes). An additional benefit of these methods is that they are expected to reduce the protein loss in subjects undergoing PD. As the methods disclosed herein allow more protein to be retained in the subject's peritoneum, this may slow down the transport of proteins from the bloodstream to the peritoneum. This would reduce the loss of protein suffered by the subject and may help prevent malnutrition, or at least avoid exacerbating any existing malnutrition suffered by the subject. Thus, there is also disclosed herein a standard washback scheme and an advanced adaptive washback scheme that seek to achieve optimised flow conditions inside the entire device.

As described above, each cycle starts from an outflow phase and continues with an inflow phase. The inflow phase has a washback phase wherein a portion of the regenerated dialysate passes through the hydrophilic fibres of the filter device, and a bypass phase wherein the remaining regenerated dialysate (the majority) directly flows back to the subject's peritoneum without passing through the hydrophilic fibres of the filter device. The filter device may be any one of the filter devices comprising the hydrophilic fibres described above, such as the filter devices 200/300/302/400/1000/1500/1501. The washback phase is needed because proteins become trapped within the hydrophilic fibres over several cycles, and the washback fluid helps in washing out these trapped proteins that clog the filter device. The volume of washback fluid (and hence duration of washback time) during the washback phase is optimised such that a minimum of spent fluid is returned to the subject, while ensuring patency of the filter is maintained for the next cycle.

A standard washback scheme may be implemented such that the amount of washback fluid is constant for each cycle. This should ensure that at least 90% of the trapped proteins are washed back to the subject and there is a maximum protein loss of less than 10% over the course of the entire therapy. Once at least 90% of the proteins are washed back, increasing the washback volume does not significantly improve the washback efficiency.

As some proteins remain trapped due to not being able to pass through the hydrophilic fibres, more proteins will accumulate over time within the hydrophilic fibres and increasingly clog the filter device. Proteins may also accumulate if the subject's protein excretion from the peritoneum is more than normal. The flow rate through the hydrophilic fibres will decrease due to greater flow resistance from the accumulated proteins, and the time taken for the entire outflow and inflow phases of subsequent cycles to complete will increase correspondingly. In this scenario, the standard washback scheme using a fixed amount of washback fluid will not be sufficient to effectively wash back all the proteins trapped in the filter device. An advanced adaptive washback scheme may be implemented instead wherein the amount of washback fluid is adjustable depending on the clogging profile of the filter device. Particularly, a filter device having clogged hydrophilic fibres may require a larger amount of washback fluid compared to a fresh filter device.

Embodiments of this advanced adaptive washback scheme can be described as a method for controlling dialysate flow in a peritoneal dialysis system. The method is performed by a processor that adjusts the amount of washback fluid based on the clogging profile of the filter device. The processor is configured to execute instructions, codes, computer programs, and/or scripts and includes suitable logic, circuitry, and/or interfaces to execute such instructions.

The method includes a step of determining a number of outflow and/or inflow parameters of a dialysate from a subject flowing between the filter device and the sorbent device over one or more cycles, each cycle having an outflow phase and an inflow phase. The parameters may include outflow rate and inflow rate of the dialysate passing through the filter device during the outflow and inflow phases, respectively. Given that the dialysate volume is fixed, one of flow rate and flow duration can be determined from the other. The flow rates can be measured using a volumetric flow rate sensor. The time taken for the dialysate to pass through the filter device and complete the respective outflow and inflow phase can be tracked using a level sensor in the reservoir. A pressure sensor can also be used to infer the flow resistance and the clogging status (e.g. by percentage of clogging) of the filter device.

The respective sensors communicate the parameters to the processor for processing, such as to derive other parameters that characterise the outflow/inflow profiles, such as flow rate, flow pressure, and flow duration. The method includes a step of comparing the parameters against a set of predefined conditions for controlling the dialysate flow through the filter device comprising the hydrophilic fibres. In this step, the processor compares the parameters against the predefined conditions using pre-programmed algorithms. Some examples of these parameters and predefined conditions are described below.

The method includes a step of apportioning, based on the comparison of the parameters, the regenerated dialysate to flow from the sorbent device to the filter device during the inflow phase, the apportioned regenerated dialysate passing through the hydrophilic fibres of the filter device. In this step, the processor calculates the amount of regenerated dialysate to apportion for the washback phase based on the comparison results.

The method includes a step of controlling a switching means or apparatus to send the apportioned regenerated dialysate to the hydrophilic fibres of the filter device (for the inflow washback phase). After the apportioned regenerated dialysate is sent, the switching means or apparatus returns the remaining regenerated dialysate to the subject without passing through the hydrophilic fibres of the filter device (for the inflow bypass phase). In this step, the processor sends a control signal to the switching means or apparatus to send the apportioned regenerated dialysate for washback. The switching means or apparatus selects between sending the regenerated dialysate to the hydrophilic fibres of the filter device or to the bypass fluid pathway.

Therefore, if the parameters meet the predefined conditions that are established based on standard parameters of a fresh or unclogged filter device, the regenerated dialysate are apportioned accordingly to adjust the amount of washback fluid. Particularly, the apportioned regenerated dialysate is larger if the filter device is clogged so as to increase the amount of washback fluid sent back to the filter device. The apportioned regenerated dialysate may be sent back at a standard flow rate from the reservoir so that the washback duration is increased, or may be sent back at a higher flow rate with the same washback duration. A higher flow rate may improve dislodging of trapped proteins from the filter device. The apportioned regenerated dialysate may be sent in various flow patterns, such as a continuous flow or a pulsatile flow. Properties affecting the flow patterns particularly for pulsatile flow (such as frequency, amplitude, and duration), may be pre-calibrated but may be adjusted based on the parameters and predefined conditions. For example, certain clogging profile of the filter device may require certain flow patterns.

The larger amount of apportioned regenerated dialysate should improve washing of the trapped proteins and clear the filter device. If one cycle is not sufficient for the adaptive washback scheme to effectively wash the filter device, the adaptive washback scheme can be implemented over multiple cycles to continually clear the filter device of trapped proteins, eventually returning to or close to the standard parameters of a fresh or unclogged filter device. The amount of regenerated dialysate for one of these multiple cycles may be apportioned based additionally on the amount of apportioned regenerated dialysate for one or more previous cycles. Using this adaptive washback scheme to continually clean the hydrophilic fibres can prolong the lifespan of the filter device.

In one example, the parameters comprise an outflow rate of the dialysate passing through the filter device during the outflow phase of a current cycle. The outflow rate can be determined from the outflow duration, or vice versa. The predefined conditions may set a standard duration for the outflow phase and for a fixed dialysate volume. The standard outflow duration may be 5 min and the corresponding washback duration is 10 sec. If the filter device is clogged, the outflow duration will increase depending on the clogging severity. If the outflow duration increases to 5.5 min, the washback duration may be increased to 15 sec. If the outflow duration increases to 6 min, the washback duration may be increased to 20 sec. Increasing the washback duration means that a larger portion of the regenerated dialysate will be sent back to the filter device as the washback fluid during the inflow phase of the current cycle.

The parameters may further comprise an outflow rate and/or an inflow rate of the dialysate passing through the filter device during the outflow phase and/or inflow phase, respectively, of a previous cycle. Consideration of the flow rates of the previous cycle, or a series of past cycles, helps to establish a clogging trend and the regenerated dialysate for subsequent cycles can be apportioned accordingly, such as depending on the increasing degree or slope of the clogging trend.

In one example, the parameters comprise the inflow rate during the inflow phase of the previous cycle and the outflow rate during the outflow phase of the current cycle. The standard durations for the inflow and outflow phases may be 2.5 min and 5 min, respectively, corresponding to a washback duration of 10 sec. If the previous inflow duration increases to 3 min and the current outflow duration increases to 5.5 min, the washback duration may be increased to 15 sec. If the previous inflow duration increases to 3.5 min and the current outflow duration increases to 7 min, the washback duration may be increased to 20 sec.

In one example, the parameters comprise the outflow rates during the outflow phases of the previous and current cycles, and the predefined conditions are associated with a difference between the outflow rates. This difference between the outflow rates represents the degree or slope of the clogging trend. If the difference exceeds a predefined threshold (such as 0.5 min or a percentage, e.g. 10%, from the previous to current cycles) and/or the current outflow duration exceeds a predefined threshold (such as 5.5 min), this means that the filter device is becoming clogged and the adaptive washback scheme is triggered to apportion the regenerated dialysate for the washback phase of the inflow phase of the current cycle.

In one example, the parameters comprise the inflow rates during the inflow phases of the previous and current cycles, and the predefined conditions are associated with a difference between the inflow rates. If the difference exceeds a predefined threshold (such as 0.5 min or a percentage, e.g. 10%, from the previous to current cycles) and/or the current inflow duration exceeds a predefined threshold (such as 3 min), the adaptive washback scheme is triggered to apportion the regenerated dialysate for the washback phase of the inflow phase of the next cycle.

Although certain values of the parameters for the predefined conditions have been described above, it will be appreciated that these parameters can have different values and these values may be interpolated according to the predefined conditions. As an example, the outflow duration of the current cycle (first cycle) is 5.5 min due to clogging and the washback duration will be adjusted to 15 sec during the inflow phase of the first cycle. The outflow duration of the next cycle (second cycle) may be reduced slightly to 5.3 min but not yet to the standard 5 min due to some residual clogging. The washback duration during the inflow phase of the second cycle will not be reduced to the standard 10 sec yet, but may instead be adjusted based on the washback duration (15 sec) for the previous cycle (first cycle). Specifically, the washback duration for the second cycle may be adjusted to an interpolated value in between, such as 13 sec.

It will also be appreciated that the predefined conditions may set different conditions for the parameters that will determine the apportioning of the regenerated dialysate. For example, the predefined conditions may consider a series of two or more previous cycles to determine a clogging trend and to apportion the regenerated dialysate accordingly. The standard parameters and predefined conditions may also be dependent on the type of hydrophilic fibres used in the filter device. For example, some hydrophilic fibres may have different standard flow rates for the filter device to operate effectively. Some hydrophilic fibres may be more vulnerable to clogging and may require stricter conditions for the adaptive washback scheme.

In addition, the modular nature of the various components of the filter device allows the flexibility for the components to be put together depending on the needs of the device. This allows a wide range of product to be obtained for various purposes. The different components of the current filter device needed for different products (non-sorbent and sorbent-based) are summarised in Tables 1 and 2, respectively.

TABLE 1

Various components of the filter device of current invention required for different products without integrated sorbent.

| Product | Component | | | |
| --- | --- | --- | --- | --- |
| | Hydrophobic fibres for degassing dialysate (e.g. 350 of device 300, FIG. 4) | Hydrophobic fibres for degassing blood (e.g. 1060 of device 1000, FIG. 12a) | Hydrophilic fibres for filtering proteins (e.g. 240 of device 200, FIG. 2; 340 of device 300, FIG. 4) | Hydrophilic fibres (as dialyser) for removal of toxins from blood (e.g. 1050 of device 1000, FIG. 13) |
| Peritoneal dialysis device with built-in degassing (e.g. device 302 of FIG. 5; device 300 of FIGS. 4 and 6) | Yes | | Yes | |
| Peritoneal dialysis device with external degassing (e.g. device 200 of FIG. 3) | | | Yes | |
| Haemodialysis device with built-in degassing (e.g. device 1500 of FIG. 12b; device 1501 of FIG. 15) | Yes | | | Yes |
| Haemodialysis device with external degassing | | | | Yes |
| Haemodialysis device with built-in degassing for ICU application (i.e. device 1000 of FIG. 13; device 1501 of FIG. 15) | Yes | Yes | | Yes |
| Haemodialysis device with external degassing for ICU application | | Yes | | Yes |

| Product | Component | |
| --- | --- | --- |
| | Post-filtration sorbent component for removal of protein bound uremic toxins (e.g. 290 of FIG. 3; 331 of device 302, FIG. 5; 380 of FIG. 6) | Hydrophobic fibres for infusing oxygen into blood and/or dialysate (e.g. 1060 of device 1000, FIG. 13; 1560 of device 1501, FIG. 15) |
| Peritoneal dialysis device with built-in degassing (e.g. device 302 of FIG. 5; device 300 of FIGS. 4 and 6) | Yes | |
| Peritoneal dialysis device with external degassing (e.g. device 200 of FIG. 3) | Yes | |
| Haemodialysis device with built-in degassing (e.g. device 1500 of FIG. 12b; device 1501 of FIG. 15) | | |
| Haemodialysis device with external degassing | | |
| Haemodialysis device with built-in degassing for ICU application (i.e. device 1000 of FIG. 13; device 1501 of FIG. 15) | | Yes |
| Haemodialysis device with external degassing for ICU application | | Yes |

TABLE 2

Various components of the filter device of current invention
required for different products with integrated sorbent.

| Product | Component | | | |
| --- | --- | --- | --- | --- |
| | Integrated sorbent (e.g. 1070 of device 1000, FIG. 13; 1570 of device 1501, FIG. 15) | Hydrophobic fibres for degassing dialysate (e.g. 350 of device 300, FIG. 4) | Hydrophobic fibres for degassing blood (e.g. 1060 of device 1000, FIG. 12a) | Hydrophilic fibres for filtering proteins (e.g. 240 of device 200, FIG. 2; 340 of device 300, FIG. 4) |
| Sorbent-based peritoneal dialysis device with built-in degassing | Yes | Yes | | Yes |
| Sorbent-based peritoneal dialysis device with external degassing | Yes | | | Yes |
| Sorbent-based haemodialysis device with built-in degassing (e.g. device 1501 of FIG. 15) | Yes | Yes | | |
| Sorbent-based haemodialysis device with external degassing | Yes | | | |
| Sorbent-based haemodialysis device with built-in degassing for ICU application (e.g. device 1000 of FIG. 13; device 1501 of FIG. 15) | Yes | Yes | Yes | |
| Sorbent-based haemodialysis device with external degassing for ICU application | Yes | | Yes | |

| Product | Component | | |
| --- | --- | --- | --- |
| | Hydrophilic fibres (as dialyser) for removal of toxins from blood (e.g. 1050 of device 1000, FIG. 13) | Post-filtration sorbent component for removal of protein bound uremic toxin (e.g. 290 of FIG. 3; 331 of device 302, FIG. 5; 380 of FIG. 6) | Hydrophobic fibres for infusing oxygen into blood and/or dialysate (e.g. 1060 of device 1000, FIG. 13; 1560 of device 1501, FIG. 15) |
| Sorbent-based peritoneal dialysis device with built-in degassing | | Yes | |
| Sorbent-based peritoneal dialysis device with external degassing | | Yes | |
| Sorbent-based haemodialysis device with built-in degassing (e.g. device 1501 of FIG. 15) | Yes | | |
| Sorbent-based haemodialysis device with external degassing | Yes | | |
| Sorbent-based haemodialysis device with built-in degassing for ICU application (e.g. device 1000 of FIG. 13; device 1501 of FIG. 15) | Yes | | Yes |
| Sorbent-based haemodialysis device with external degassing for ICU application | Yes | | Yes |

The invention claimed is:

1. A device for use in peritoneal dialysis consisting of:
   (i) a filter device; and
   (ii) a post-filtration system,
wherein the filter device comprises:
   a housing comprising a first port and a second port; and
   a hollow fibre membrane formed from hollow hydrophilic fibres within the housing, where each of the fibres have an inner surface and an outer surface, wherein
   the hollow hydrophilic fibres comprise a porous wall matrix; and
   the inner surface of the hollow hydrophilic fibres are aligned co-axially with respect to the alignment of the first port and the outer surface of the hollow fibres is aligned perpendicularly with respect to the alignment of the second port, such that, when used:
   a dialysate from a subject enters the filter device through the first port is filtered through the porous wall matrix, and the filtered dialysate exits via the second port in an outflow direction; and
   a regenerated dialysate from a sorbent system enters the filter device through the second port, passes through the porous wall matrix, and exits via the first port in an inflow direction,
and wherein the post-filtration system consists of:
   (a) a switch;
   (b) a post-filtration sorbent compartment; and
   (c) fluid connections connecting the post-filtration sorbent compartment, the switch and the first port of the housing,
wherein the post-filtration system and filter device together form:
   a first fluid pathway consisting of the first port of the housing, the switch and a fluid connection therebetween; and a second fluid pathway consisting of the first port of the housing, the switch, the post-filtration sorbent compartment, and a fluid connection therebetween;
where the switch is suitable for selecting between the first and second fluid pathways,
where the first and second fluid pathways are both fluidly connected to the first port of the housing via the switch,
where the post-filtration sorbent compartment comprises a post-filtration sorbent that is suitable for removing one or more of water-soluble uremic toxins, protein-bound uremic toxins, low-molecular weight proteins, endotoxins, exotoxins, inflammatory mediators and microorganisms.

2. The device according to claim 1, wherein first fluid pathway is connectable to the subject's peritoneum via the switch; and
   the second fluid pathway is connectable to the subject's peritoneum via the post-filtration sorbent compartment.

3. The device of claim 1, further comprising,
   a sorbent device,
wherein
   the filter device is arranged to receive and filter the entirety of dialysate from the subject and to provide the filtered dialysate to the sorbent device when operated in an outflow direction; and
   the filter device is arranged to receive at least part of the regenerated dialysate from the sorbent device when operated in an inflow direction.

4. The device of claim 3, wherein the device further comprises a bypass means or apparatus, which comprises:
   a bypass fluid pathway connected to the sorbent device and arranged to return a regenerated dialysate to the subject without passing through the filter device; and
   a switching means or apparatus that selects between sending a regenerated dialysate to the filter device or to the bypass fluid pathway.

* * * * *